(12) United States Patent
Caspers

(10) Patent No.: US 6,761,742 B2
(45) Date of Patent: *Jul. 13, 2004

(54) VACUUM PUMP AND SHOCK ABSORBER FOR ARTIFICIAL LIMB

(75) Inventor: Carl A. Caspers, Avon, MN (US)

(73) Assignee: Otto Bock HealthCare LP, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/059,990

(22) Filed: Jan. 29, 2002

(65) Prior Publication Data

US 2002/0087215 A1 Jul. 4, 2002

Related U.S. Application Data

(63) Continuation of application No. 09/534,274, filed on Mar. 23, 2000, now Pat. No. 6,554,868, which is a continuation-in-part of application No. 09/325,297, filed on Jun. 3, 1999, now abandoned.

(51) Int. Cl.7 .............................. A61F 2/80; A61F 2/74
(52) U.S. Cl. .......................................... 623/34; 623/35
(58) Field of Search ..................................... 623/32–37

(56) References Cited

U.S. PATENT DOCUMENTS

| | | | |
|---|---|---|---|
| 980,457 A | | 1/1911 | Toles |
| 2,424,278 A | | 7/1947 | Kunkel |
| 2,464,443 A | * | 3/1949 | Ganoe et al. ............. 623/26 X |
| 2,530,285 A | * | 11/1950 | Catranis ...................... 623/44 |
| 2,533,404 A | | 12/1950 | Sharp et al. |
| 2,606,325 A | | 8/1952 | Nelson et al. |
| 2,664,572 A | | 1/1954 | Blevens |
| 2,671,225 A | | 3/1954 | Schoene et al. |

(List continued on next page.)

FOREIGN PATENT DOCUMENTS

| | | |
|---|---|---|
| AU | 670631 | 6/1995 |
| BE | 675386 | 5/1966 |
| CA | 2098945 | 4/1994 |
| DE | 745981 | 5/1944 |

(List continued on next page.)

OTHER PUBLICATIONS

Solomons, Organic Chemistry (6th ed.), John Wiley & Sons, Inc., New York, 1996, pp. 853–854.
Waterproof/Windproof/Breathable—How it Works, Sympa Tex Technologies GmbH Data Sheets, 5 pages.
Technology—How do they Work? SealSkinz Web Pages, 4 pages.
Gore–Tex Web Page, 2 pages.
Gill Web Page, 2 pages.

Primary Examiner—David H. Willse
(74) Attorney, Agent, or Firm—Faegre & Benson, LLP

(57) ABSTRACT

A weight-actuated vacuum pump for a hypobarically-controlled artificial limb having a socket with a cavity to receive a residual limb. A dual-action pump has a housing fixedly attached to the socket of the artificial limb, a cylinder reciprocating within the housing and attached to the pylon of the artificial limb, a first chamber within the cylinder, a piston reciprocating within the first chamber, a second chamber between the cylinder and the housing, and valve means for connecting the first chamber and second chamber to the cavity and to atmosphere. A single-action pump has a housing fixedly attached to the pylon of the artificial limb with a first chamber therein, a piston reciprocating in the first chamber with a seal, forming a second chamber between the piston and the housing, an intake/exhaust port connected to the second chamber, and one-way valves connecting the second chamber to the cavity and to atmosphere. Ambulation causes the vacuum pump, under the influence of the wearer's body weight, to draw air out of the cavity, producing a vacuum within the cavity.

34 Claims, 16 Drawing Sheets

U.S. PATENT DOCUMENTS

| | | |
|---|---|---|
| 2,696,010 A | 12/1954 | Robinson |
| 2,696,011 A | 12/1954 | Galdik |
| 2,790,180 A | 4/1957 | Hauser |
| 2,808,593 A | 10/1957 | Anderson |
| 3,253,600 A | 5/1966 | Scholl |
| 3,322,873 A | 5/1967 | Hitchcock |
| 3,377,416 A | 4/1968 | Kandel |
| 3,393,407 A | 7/1968 | Kandel |
| 3,557,387 A | 1/1971 | Ohlenbusch et al. |
| 3,631,542 A | 1/1972 | Potter |
| 3,712,298 A | 1/1973 | Snowdon et al. |
| 3,732,578 A | 5/1973 | Pollack |
| 3,751,733 A | 8/1973 | Fletcher et al. |
| 3,858,379 A | 1/1975 | Graves et al. |
| 3,895,405 A | 7/1975 | Edwards |
| 3,975,350 A | 8/1976 | Hudgin et al. |
| 3,991,424 A | 11/1976 | Prahl |
| 4,283,800 A | 8/1981 | Wilson |
| 4,314,398 A | 2/1982 | Pettersson |
| 4,381,768 A | 5/1983 | Erichsen et al. |
| 4,404,296 A | 9/1983 | Schapel |
| 4,456,642 A | 6/1984 | Burgdorfer et al. |
| 4,466,936 A | 8/1984 | Schapel |
| 4,479,272 A | 10/1984 | Belzisky |
| 4,623,354 A | 11/1986 | Childress et al. |
| 4,634,446 A | 1/1987 | Kristinsson |
| 4,635,626 A | 1/1987 | Lerman |
| 4,704,129 A | 11/1987 | Massey |
| 4,822,371 A | 4/1989 | Jolly et al. |
| 4,828,325 A | 5/1989 | Brooks |
| 4,888,829 A | 12/1989 | Kleinerman et al. |
| 4,908,037 A | 3/1990 | Ross |
| 4,923,475 A | 5/1990 | Gosthnian et al. |
| 5,007,937 A | 4/1991 | Fishman et al. |
| 5,108,455 A | 4/1992 | Telikicheria |
| 5,133,776 A | 7/1992 | Crowder |
| 5,139,523 A | 8/1992 | Paton et al. |
| 5,163,965 A | 11/1992 | Rasmusson et al. |
| 5,211,667 A | 5/1993 | Danforth |
| 5,221,222 A | 6/1993 | Townes |
| 5,258,037 A | 11/1993 | Caspers |
| 5,314,497 A | 5/1994 | Fay et al. |
| 5,362,834 A | 11/1994 | Schapel et al. |
| 5,376,129 A | 12/1994 | Faulkner et al. |
| 5,376,131 A | 12/1994 | Lenze et al. |
| 5,376,132 A | 12/1994 | Caspers |
| 5,397,628 A | 3/1995 | Crawley et al. |
| 5,507,834 A | 4/1996 | Laghi |
| 5,534,034 A | 7/1996 | Caspers |
| 5,549,709 A | 8/1996 | Caspers |
| 5,571,208 A | 11/1996 | Caspers |
| 5,593,454 A | 1/1997 | Helmy |
| 5,658,353 A | 8/1997 | Layton |
| 5,702,489 A | 12/1997 | Slemker |
| 5,728,167 A | 3/1998 | Lohmann |
| 5,728,168 A | 3/1998 | Laghi et al. |
| 5,728,169 A | 3/1998 | Norvell |
| 5,728,170 A | 3/1998 | Becker et al. |
| 5,735,906 A | 4/1998 | Caspers |
| 5,830,237 A | 11/1998 | Kania |
| 5,888,216 A | 3/1999 | Haberman |
| 5,888,230 A | 3/1999 | Helmy |
| 5,888,231 A | 3/1999 | Sandvig et al. |
| 5,904,721 A | 5/1999 | Henry et al. |
| 5,904,722 A | 5/1999 | Caspers |
| 6,063,125 A | 5/2000 | Arbogast et al. |
| D429,335 S | 8/2000 | Caspers |
| 6,117,177 A | 9/2000 | Chen et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 2001/0005798 A1 | 6/2001 | Caspers |

FOREIGN PATENT DOCUMENTS

| | | |
|---|---|---|
| DE | 2712342 | 9/1977 |
| DE | 2729800 | 1/1979 |
| DE | 3221920 | 4/1983 |
| DE | 4217877 | 12/1992 |
| DE | 4321182 | 12/1994 |
| DE | 9418210.8 | 3/1995 |
| DE | 9419211.1 U1 | 3/1995 |
| DE | 9417913.1 U1 | 4/1995 |
| DE | 29905020 | 7/1999 |
| DK | DE-3221920 | 4/1983 |
| EP | 0019612 | 11/1980 |
| EP | 0057838 | 8/1982 |
| EP | 0057839 | 8/1982 |
| EP | 0086147 | 8/1983 |
| EP | 0261884 | 3/1988 |
| EP | 0320170 | 6/1989 |
| EP | 0363654 | 4/1990 |
| EP | 0631765 | 1/1995 |
| EP | 0650708 | 5/1995 |
| EP | 0870485 | 10/1998 |
| FR | 1135516 | 9/1960 |
| FR | 1532625 | 7/1968 |
| FR | 2420335 | 10/1979 |
| FR | 2501999 | 9/1982 |
| GB | 136504 | 1/1920 |
| GB | 267988 | 3/1927 |
| GB | 2069847 | 9/1981 |
| GB | 2149309 | 6/1985 |
| JP | 7155343 | 6/1995 |
| RU | 1771722 | 10/1992 |
| RU | 1812982 | 4/1993 |
| RU | 1821177 | 6/1993 |
| SU | 1771722 | 10/1992 |
| SU | 1812982 | 4/1993 |
| SU | 1821177 | 6/1993 |
| WO | WO-84/00881 | 3/1984 |
| WO | WO 95/05792 | 3/1995 |
| WO | WO 96/21405 | 7/1996 |
| WO | WO 98/04218 | 2/1998 |
| WO | WO 98/55055 | 12/1998 |
| WO | WO 99/65434 | 12/1999 |
| WO | WO 00/03665 | 1/2000 |
| WO | WO 00/74611 | 12/2000 |
| WO | WO-01/54631 | 8/2001 |
| WO | WO-01/70147 | 9/2001 |

\* cited by examiner

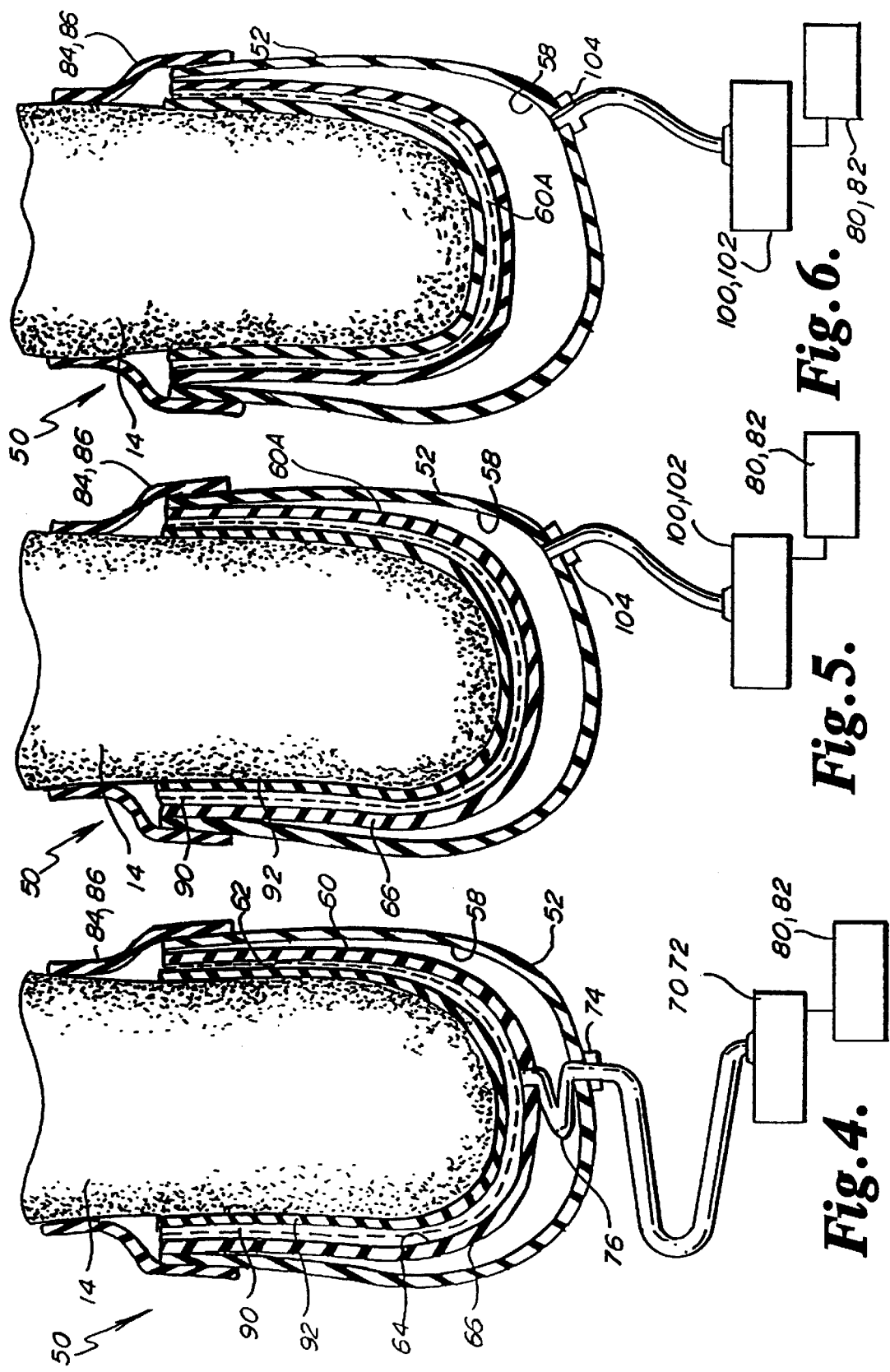

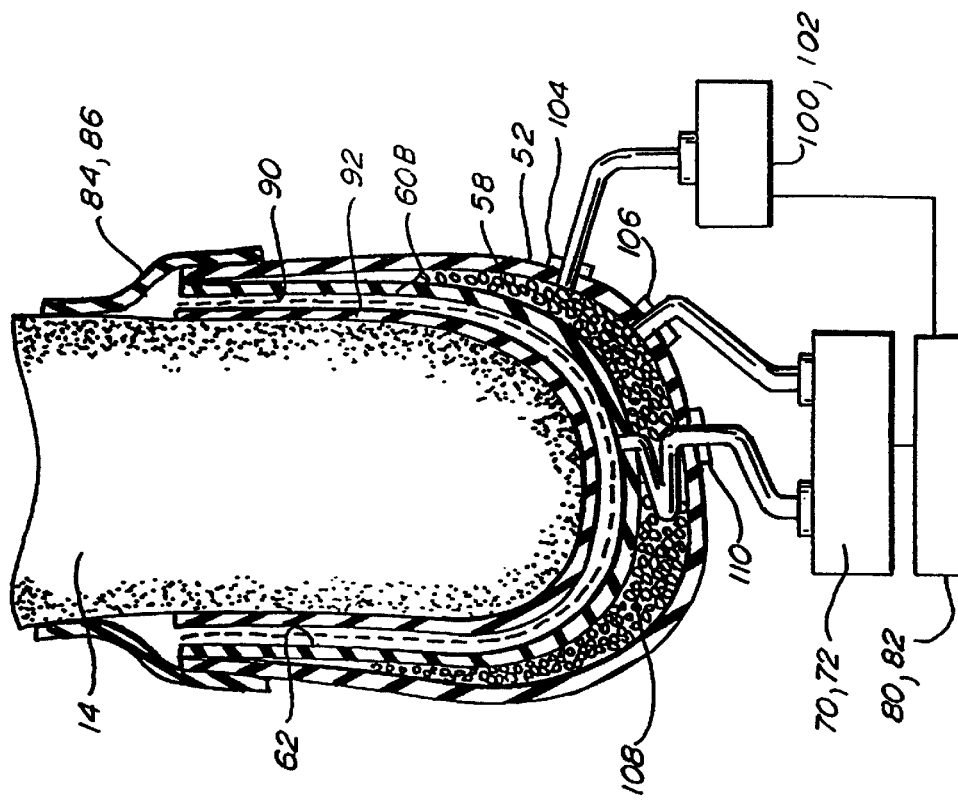
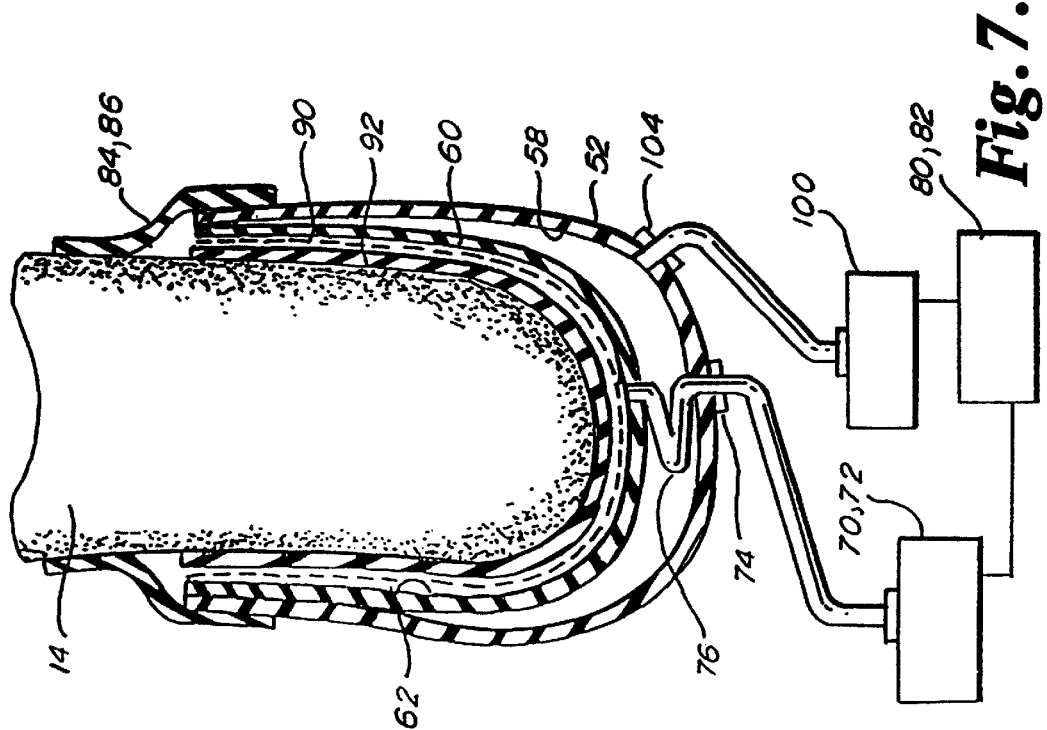

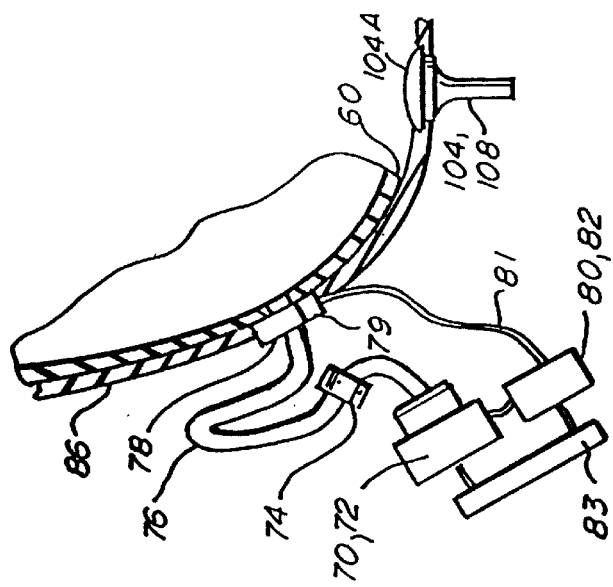
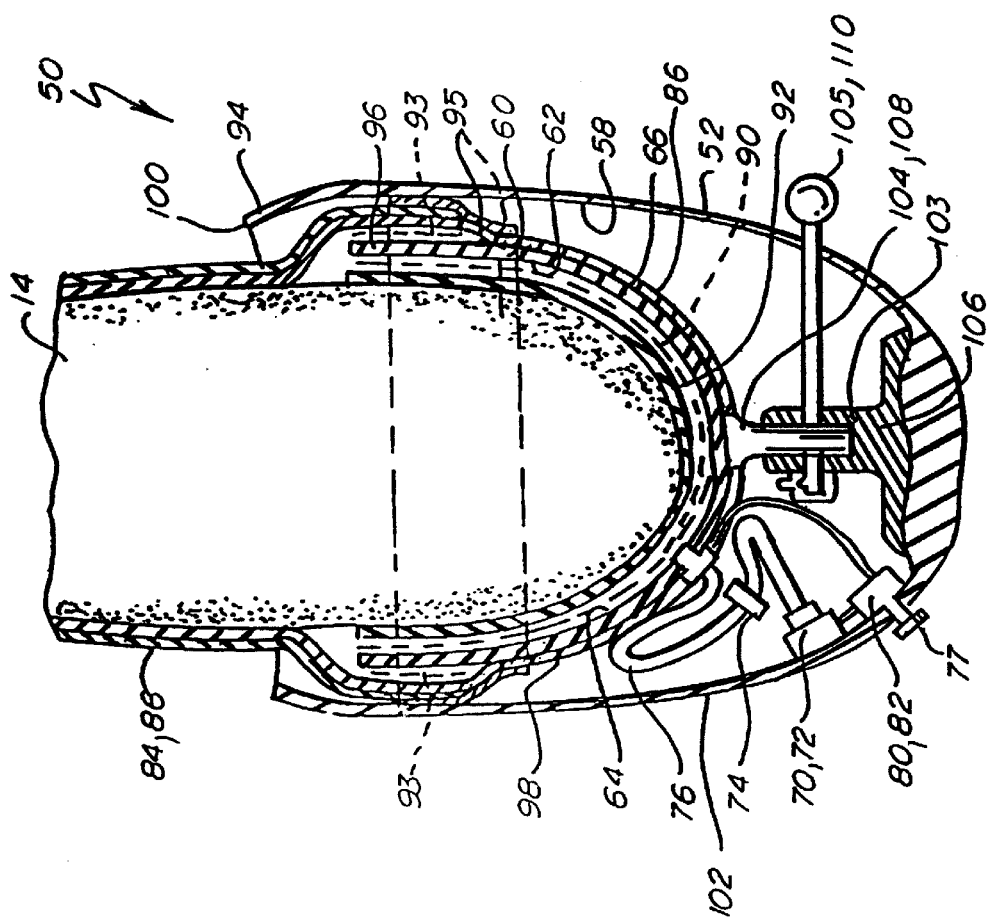

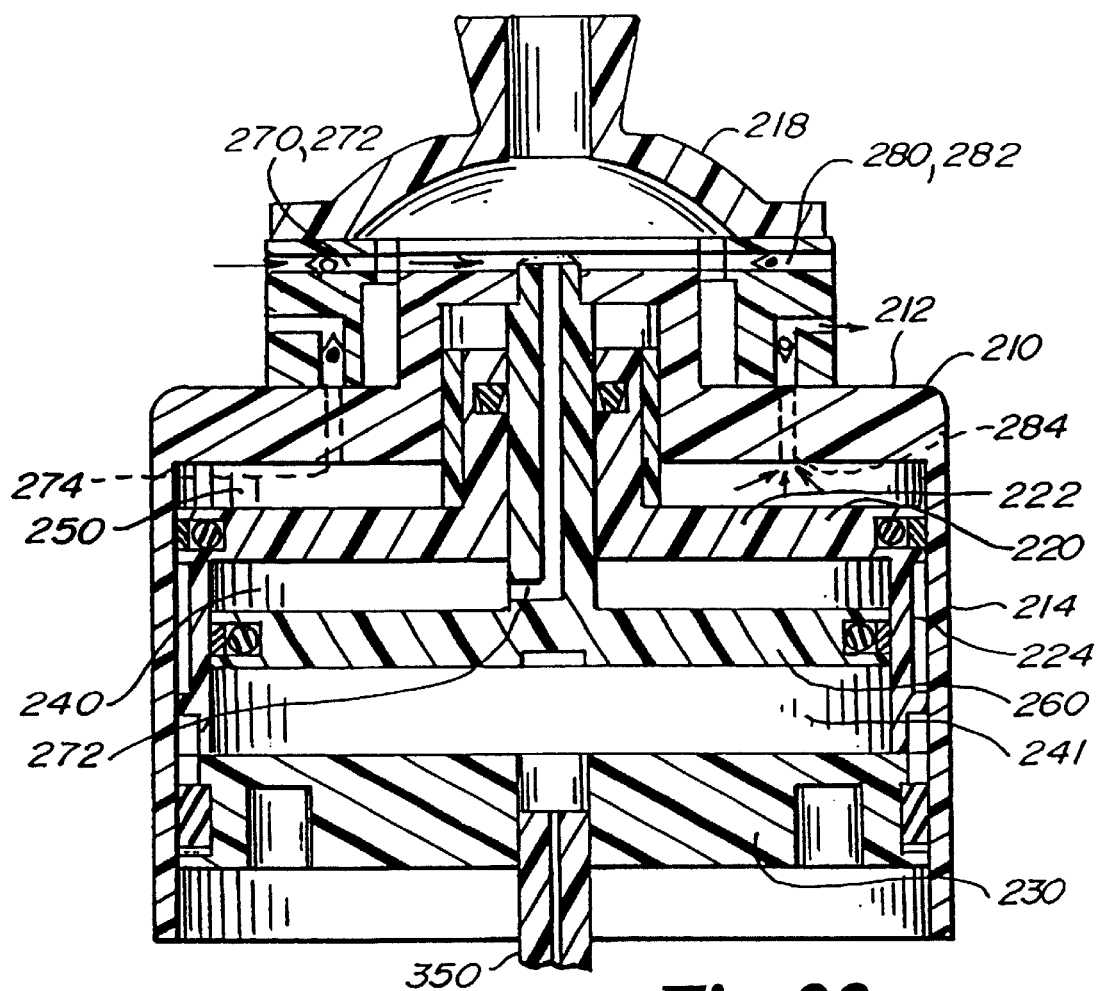
Fig.23.
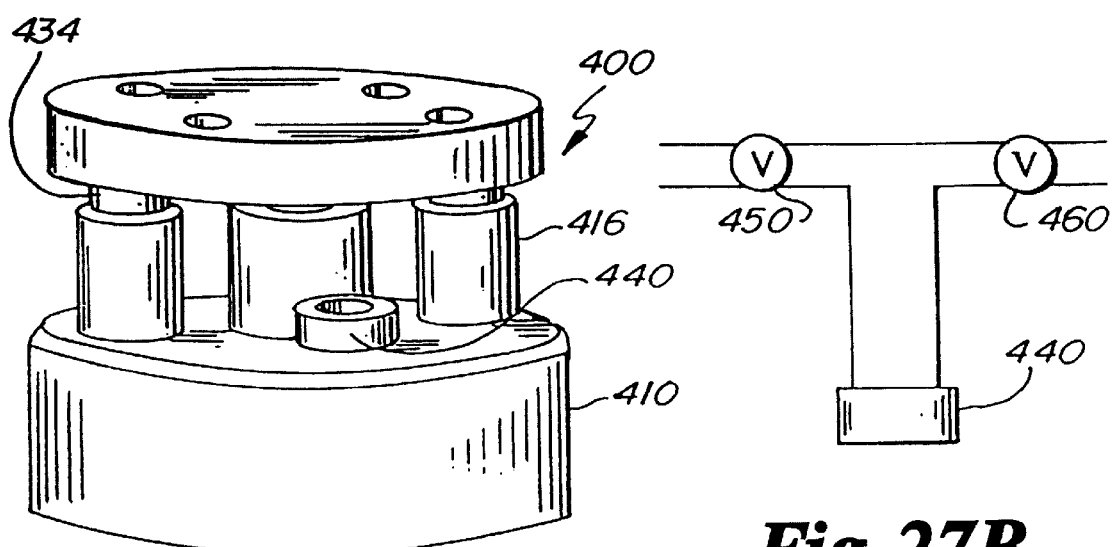
Fig.27A.
Fig.27B.

VACUUM PUMP AND SHOCK ABSORBER FOR ARTIFICIAL LIMB

This is a continuation of application Ser. No. 09/534,274, filed Mar. 23, 2000, now U.S. Pat. No. 6,554,868, which is a continuation-in-part of abandoned application Ser. No. 09/325,297, filed Jun. 3, 1999, now abandoned.

BACKGROUND OF THE INVENTION

The present invention relates to prosthetic devices and more particularly to a hypobarically-controlled artificial limb for amputees.

An amputee is a person who has lost part of an extremity or limb such as a leg or arm which commonly may be termed as a residual limb. Residual limbs come in various sizes and shapes with respect to the stump. That is, most new amputations are either slightly bulbous or cylindrical in shape while older amputations that may have had a lot of atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

Referring to FIGS. 1 and 2, a below the knee residual limb 10 is shown and described as a leg 12 having been severed below the knee terminating in a stump 14. In this case, the residual limb 10 includes soft tissue as well as the femur 16, knee joint 18, and severed tibia 20 and fibula 22. Along these bone structures surrounded by soft tissue are nerve bundles and vascular routes which must be protected against external pressure to avoid neuromas, numbness and discomfort as well as other kinds of problems. A below the knee residual limb 10 has its stump 14 generally characterized as being a more bony structure while an above the knee residual limb may be characterized as including more soft tissue as well as the vascular routes and nerve bundles.

Referring to FIG. 2, amputees who have lost a part of their arm 26, which terminates in a stump 28 also may be characterized as having vascular routes, nerve bundles as well as soft and bony tissues. The residual limb 10 includes the humerus bone 30 which extends from below the shoulder to the elbow from which the radius 34 and ulna 36 bones may pivotally extend to the point of severance. Along the humerus bone 30 are the biceps muscle 38 and the triceps muscle 40 which still yet may be connected to the radius 34 and the ulna, 36, respectively.

In some respects, the residual limb amputee that has a severed arm 26 does not have the pressure bearing considerations for an artificial limb but rather is concerned with having an artificial limb that is articulable to offer functions typical of a full arm, such as bending at the elbow and grasping capabilities. An individual who has a paralyzed limb would also have similar considerations wherein he or she would desire the paralyzed limb to having some degree of mobility and thus functionality.

Historically, artificial limbs typically used by a leg amputee were for the most part all made out of wood such as an Upland Willow. The limbs were hand carved with sockets for receiving the stump 14 of the residual limb 10. Below the socket would be the shin portion with the foot below the shin. These wooden artificial limbs were covered with rawhide which often were painted. The sockets of most wood limbs were hollow as the limbs were typically supported in the artificial limb by the circumferential tissue adjacent the stump 14 rather than at the distal end of the stump 14.

Some artificial limbs in Europe were also made from forged pieces of metal that were hollow. Fiber artificial limbs were also used which were stretched around a mold after which they were permitted to dry and cure. Again, these artificial limbs were hollow and pretty much supported the residual limb about the circumferential tissue adjacent the stump 14.

All of these various artificial limbs have sockets to put the amputee's stump 14 thereinto. There are generally two categories of sockets. There are hard sockets wherein the stump goes right into the socket actually touching the socket wall without any type of liner or stump sock. Another category of sockets is a socket that utilizes a liner or insert. Both categories of sockets typically were opened ended sockets where they had a hollow chamber in the bottom and no portion of the socket touched the distal end of the stump 14. So, the stump was supported about its circumferential sides as it fits against the inside wall of the sockets.

These types of sockets caused a lot of shear force on the stump 14 as well as had pressure or restriction problems on the nerve bundles and vascular flow of fluid by way of the circumferential pressure effect of the socket on the limb. This pressure effect could cause a swelling into the ends of the socket where an amputee may develop severe edema and draining nodules at the end of their stump 14.

With time, prosthetists learned that by filling in the socket's hollow chamber and encouraging a more total contact with the stump and the socket, the swelling and edema problems could be eliminated. However, the problematic tissue configurations, such as bony prominences, required special consideration such as the addition of soft or pliable materials to be put into the socket.

Today, most artificial limbs are constructed from thermoset plastics such as polyester resins, acrylic resins, polypropylenes and polyethylenes, which are perhaps laminated over a nylon stockinette which also may be impregnated by the various resins.

In the past, most artificial limbs were suspended from the amputee's body by some form of pulley, belt or strap suspension often used with various harnesses and perhaps leather lacers or lacings. Another method of suspending artificial limbs is known as the wedge suspension wherein an actual wedge is built into the socket which is more closed at its top opening. The wedge in the socket cups the medial femoral condyle or knuckle at the abductor tubical. Yet another form of suspension is referred to as the shuttle system or a mechanical hookup or linkup wherein a thin suction liner is donned over the stump that has a docking device on the distal end which mechanically links up with its cooperative part in the bottom of the socket chamber. Sleeve suspensions were also used wherein the amputee may use a latex rubber tube which forms into a rubber-like sleeve which would be rolled on over both the top of the artificial limb and onto the amputee's thigh. The sleeve suspensions have been used in combination with other forms of suspensions techniques.

Both the use of a positive pressure system and the use of a negative pressure system (or hypobaric closed chamber) have been utilized in the field of prosthetics. At one time, for pressure systems "inflatable inner tubes" were used to fit into sockets. Presently, there are pneumatic "bags" which are strategically placed over what people consider to be good weight-bearing areas to increase pressure to help accommodate for volume changes within the socket.

The problem with this is that it is a very specific pressure and creates atrophy and loss of tissue dramatically over these high pressure areas. None of these systems employs positive pressure distributed over the total contact area between the residual limb and the artificial limb socket to accommodate volume changes within the socket.

The negative pressure aspects have been utilized for a closed chamber in that a socket is donned by pulling in with a sock, pulling the sock out of the socket and then closing the opening with a valve. This creates a seal at the bottom and the stump is held into the socket by the hypobaric seal. However, there are no systems that employ a negative pressure produced by a vacuum pump to lock the residual limb to the artificial limb.

The older systems were initially started in Germany. They were an open-ended socket, meaning there was an air chamber in the bottom of the socket. This did not work particularly well because it would cause swelling of the residual limb into the chamber created by the negative draw of suspending the weight of the leg and being under a confined area. This would lead to significance edema which would be severe enough to cause stump breakdown and drainage.

It was later discovered in America that total contact was essential between the residual limb and the socket and once you had total contact the weight was distributed evenly or the suspension was distributed over the whole surface of the limb rather than just over the open chamber portion of the socket.

The human body as a whole is under approximately one atmosphere of pressure at sea level. It keeps and maintains a normal fluid system throughout the body. When an amputee dons a prosthesis and begins taking the pressures of transmitting the weight of the body through the surface area of the residual limb to the bone, there is increased pressure on the residual limb equal to one atmosphere plus whatever additional pressures are created by weight bearing. This increased pressure causes the eventual loss of fluids within the residual limb to the larger portion of the body which is under less pressure. This loss of fluids causes the volume of the residual limb to decrease during the day. It varies from amputee to amputee, but it is a constant among all amputee and the more "fleshy" and the softer the residual limb, the more volume fluctuation there will be. The greater the weight and the smaller the surface area, the greater the pressures will be and the more "swings" there will be in fluids. In the past, the amputee had to compensate for this volume decrease by removing the artificial limb and donning additional stump socks to make up for the decreased residual limb volume.

While some of these devices addressed some of the problems associated with prosthetics, none of the artificial limbs, liners and socket, individually or in combination, offered a prosthesis that presented a total contact relationship with the residual limb; absorbed and dissipated shear, shock and mechanical forces transmitted to the limb tissues by the artificial limb; controlled residual limb volume; and used negative pressure as a locking device to hold the residual limb into the socket.

There is a need for an improved hypobarically-controlled artificial limb that will offer total contact relationship with the residual limb; absorb and dissipate shock, mechanical and shear forces typically associated with ambulation, twisting and turning and weight bearing with an artificial limb; control residual limb volume by way of even weight distribution; use negative pressure as a locking device to hold the residual limb into the socket; and to totally adjust and adapt the internal socket environment to changes in residual limb volume; and control stump volume changes by a negative pressure system which is also capable of providing positive pressure. Ideally, the vacuum system should be automatically regulated.

There is also a need for an improved hypobarically-controlled artificial limb with a positive mechanical interlock between an inner socket, which receives the residual limb, and an outer socket which attaches to the shin and foot of the artificial limb. Both the inner socket and the outer socket should have a rigid lower portion for weight-bearing and a substantially flexible upper portion to allow movement of the residual limb.

In the past, artificial limbs had to be custom-built for the amputee. The custom building process generally consisted of: placing a singly ply thin cotton casting sock over the residual limb; making a first negative mold of the residual limb for forming an orthopedic plaster wrap about the residual limb and casting sock; making a first positive model of the residual limb by filling the negative mold with plaster; forming a thermoplastic foam about the positive model to create a space for a liner; adding additional thermoplastic foam to form a distal end cap as well as other areas which may require additional thicknesses due to tissue configurations; forming a second enlarged negative plaster mold about the foam; removing the foam; pouring a liquid and moldable liner into the space between the positive model and the second negative mold; allowing the liner to harden; removing the liner from the second negative mold; having the amputee don the liner over the residual limb; placing another single ply thin casting sock over the liner; making a third plaster wrap or negative mold of the artificial limb socket about the residual limb and the liner; removing the liner from the third plaster wrap; making a plaster cast or positive model of the socket from dental plaster; milling or shaving the positive model to create a reduced positive model to create weight bearing areas and compression of the liner against the residual limb and the socket; and making the socket from the reduced positive model.

This custom-building process is expensive, time-consuming, and requires the constant attention of a skilled prosthetist.

There is a need for a generic artificial limb socket which can be fitted to the contours of the residual limb without the need for a lengthy, expensive custom-molding process. The socket should contain a semi-compressible molding material which can be molded to the contours of the residual limb under vacuum and/or positive air pressure.

SUMMARY OF THE INVENTION

A principle object and advantage of the present invention is that it uses vacuum within the artificial limb socket to suspend the artificial limb from the residual limb.

Another object and advantage of the present invention is that it uses vacuum within the artificial limb socket to assist in socket fit and minimizes volumetric limb changes within the socket.

Another object and advantage of the present invention is that it uses vacuum within the socket to lock the residual limb into the socket while preventing negative draw within the socket from causing swelling of the residual limb into the socket.

Another object and advantage of the present invention is that it uses vacuum within the socket to oppose the loss of fluids from the residual limb caused by weight-bearing pressures.

Another object and advantage of the present invention is that it uses vacuum pressure to lock the residual limb into the socket and reduce socket volume to compensate for fluid loss in the residual limb.

Another object and advantage of the present invention is that both vacuum and positive pressure may be created by a miniaturized pump with a mechanical or motor drive.

Another object and advantage of the present invention is that it includes a digital computer system to control the miniaturized pump to regulate both negative pressure and positive pressure, when used.

Another object and advantage of the present invention is that is includes a semi-compressible molding material between the outer socket and the inner socket which may be molded to the contours of the artificial limb under the influence of vacuum pressure, thereby avoiding the need for a custom-building process.

Another object and advantage of the present invention is that the inner socket and outer socket are interlockable with each other to prevent relative movement. The interlocking may be achieved by any of a variety of mechanisms, such a pins or detents. The inner socket is removable from the outer socket.

Another object and advantage of the present invention is that vacuum pump and the vacuum regulator may be enclosed in the space between the outer socket and the inner socket, thereby preventing damage to these components. The vacuum regulator may be controlled by an externally-accessible vacuum control.

Another object and advantage of the present invention is that both the inner socket and the outer socket may be constructed of a lower, rigid portion and an upper substantially flexible portion. The lower rigid portion provides the necessary rigidity to support the person's weight, while the upper flexible portion accommodates movement of the residual limb.

Another object and advantage of the present invention is that it includes an outer sheath between the inner socket and the suspension sleeve, to prevent abrasion of the suspension sleeve by the inner socket.

Another principal object and advantage of the present invention is that it may comprise only a single socket, rather than two sockets, simplifying construction and reducing cost and complexity.

Another principal object and advantage of the present invention is that it includes a large vacuum reservoir that can be used to maintain vacuum in the cavity between the residual limb or liner and the socket as air leaks into the cavity.

Another principal object and advantage of the present invention is that it includes a weight-activated vacuum pump that automatically maintains vacuum in the cavity as the wearer walks on the artificial limb.

BRIEF DESCRIPTION OF THE DRAWINGS

FIG. 4 is a cross-section of the artificial limb in FIG. 3, which is a first embodiment of the artificial limb;

FIG. 5 is a cross-section of the artificial limb similar to FIG. 4, showing a second embodiment of the artificial limb;

FIG. 6 is the same as FIG. 5, but showing compression of the inner socket under the influence of positive air pressure;

FIG. 7 is a cross-section of the artificial limb showing a third embodiment of the artificial limb;

FIG. 8 is a cross-section of the artificial limb showing a fourth embodiment of the artificial limb;

FIG. 13 is a cross-section of the artificial limb showing a seventh embodiment of the artificial limb;

FIG. 14 is a detailed view of the vacuum mechanism and suspension sleeve of FIG. 13;

FIG. 23 is the same as FIG. 22, except that the wearer's weight is being applied to the pylon of the artificial limb;

FIG. 27A is an side perspective view of a second embodiment of a weight-actuated vacuum pump and shock absorber.

FIG. 27B is a schematic of the intake/exhaust port and one-way valves of this embodiment;

DESCRIPTION OF THE PREFERRED EMBODIMENT

Figure 1:
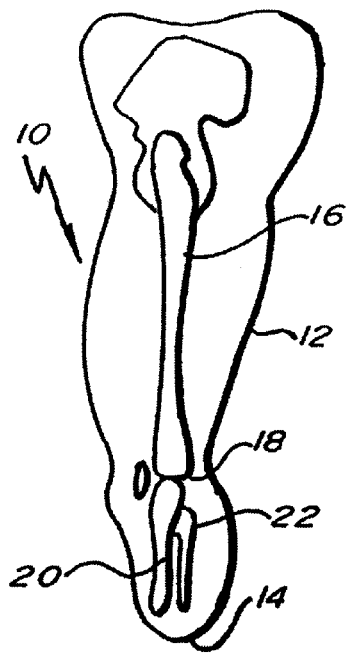
FIG. 1 is a side elevational view of the tissue and skeletal structure of an amputee's residual limb.
Figure 2:
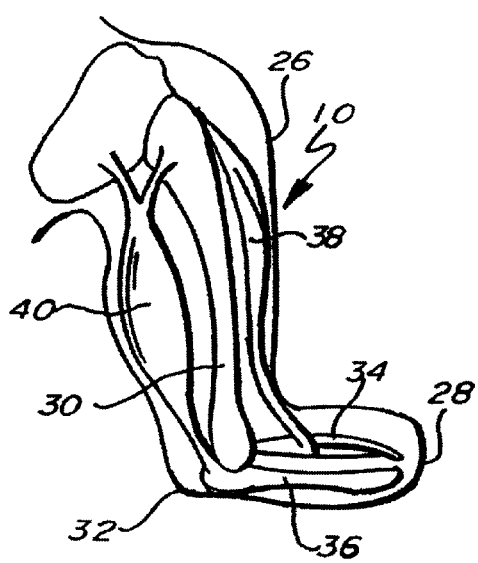
FIG. 2 is a side elevational view of a residual limb in the form of an amputated arm showing the skeletal and muscular structure of the residual limb.
Figure 9:
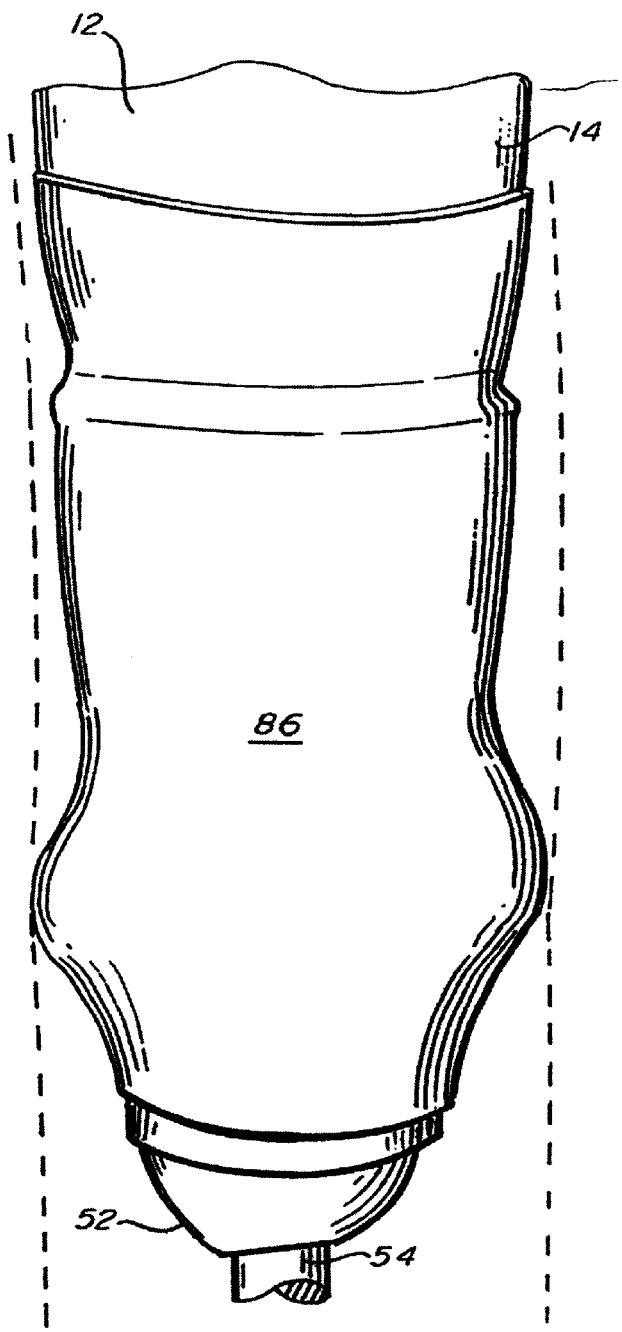
FIG. 9 is an elevational view of the polyurethane sleeve and second stretchable nylon sleeve rolled over the socket and residual limb with clothing shown in broken outline.
Figure 3:
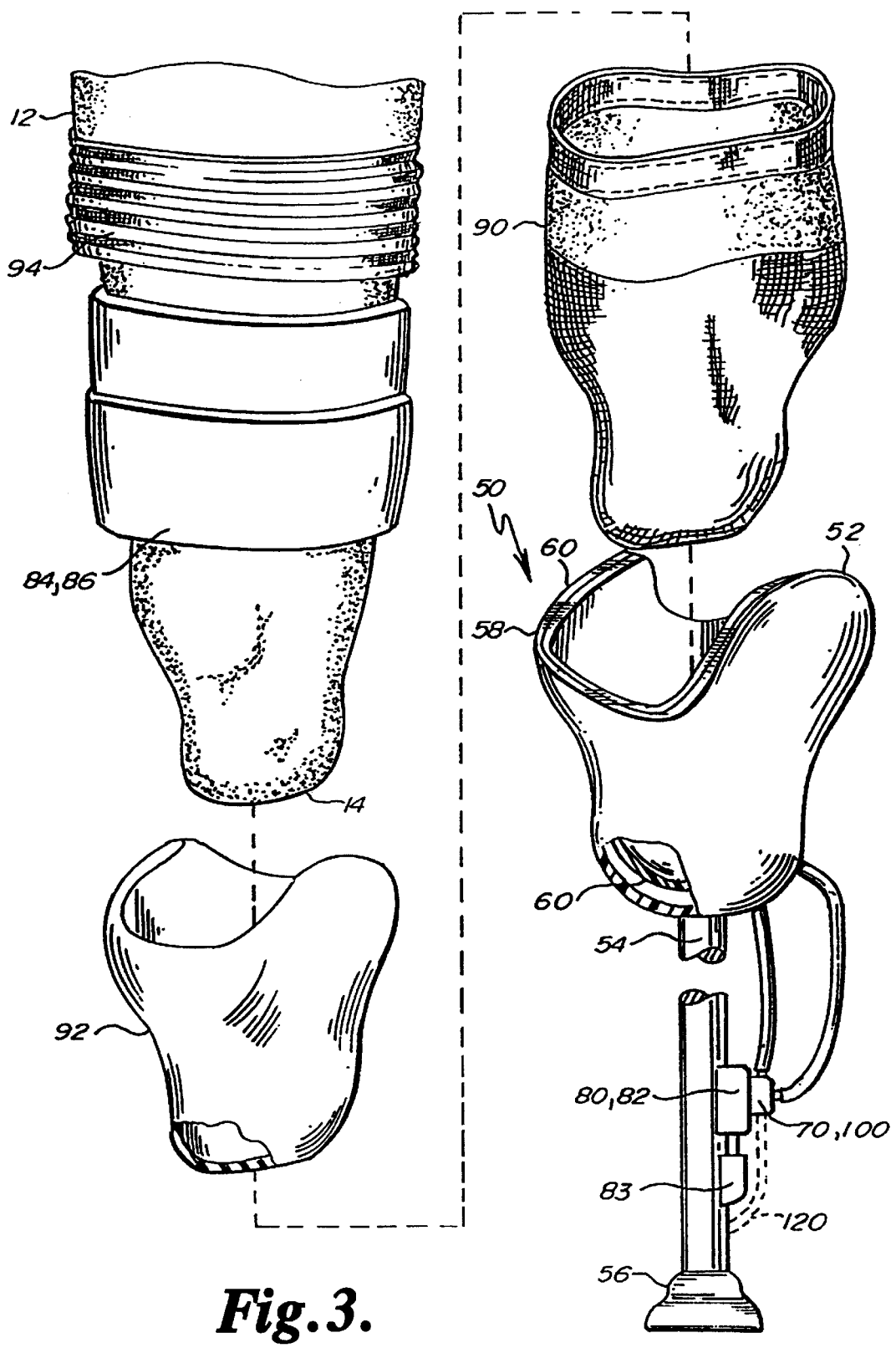
FIG. 3 is an exploded elevational view of the residual limb donning the polyurethane sleeve, stretchable nylon sleeve, liner, nylon sheath and socket of an artificial limb.

FIG. 3 shows the hypobarically-controlled artificial limb 50 of the present invention. The hypobarically-controlled artificial limb 50 includes an outer socket 52, shin 54, and foot 56. The outer socket 52 has a volume and shape to receive a substantial portion of the residual limb 14 with a space 58 therebetween.

A first embodiment of the hypobarically-controlled artificial limb 50 is shown in FIG. 4. The hypobarically-controlled artificial limb 50 further includes a flexible inner socket 60 with a cavity 62 with a volume and shape for receiving a substantial portion of the residual limb 14 and fitting in the space 58 between the outer socket 52 and the residual limb 14. The inner socket 60 has an inner surface 64 opposing the residual limb 14 and an outer surface 66 opposing the outer socket 52.

A vacuum source 70 may conveniently be attached to the shin or pylon 54. The vacuum source 70 may preferably be a mechanical or motor-driven pump 72. The vacuum source 70 is connected to a power source 83, which may be a battery.

A vacuum valve 74 is suitably connected to the vacuum source 70. The vacuum valve 74 may preferably be disposed on the outer socket 52. A vacuum tube 76 connects the vacuum valve 74 to the cavity 62. It will be seen that the vacuum source will cause the residual limb 14 to be drawn into firm contact with the inner surface 64 of the inner socket 60.

The hypobarically-controlled artificial limb 50 also includes a regulator means 80 for controlling the vacuum source 70. Preferably, the regulator means 80 may be a digital computer 82. Alternately, the regulator means may be a vacuum regulator. The regulator means 80 is connected to a power source 83, which may be a battery.

A seal means 84 makes an airtight seal between the residual limb 14 and the outer socket 52. Preferably, the seal means 84 is a nonfoamed, nonporous polyurethane suspension sleeve 86 which rolls over and covers the outer socket 52 and a portion of the residual limb 14. Alternatively, the seal means 84 may be any type of seal which is airtight.

The hypobarically-controlled artificial limb 50 may also include a thin sheath 90 between the residual limb 14 and the inner surface 64 of the inner socket 60. As vacuum is applied to the cavity 62, the sheath 90 will allow the vacuum to be evenly applied throughout the cavity 62. Without the sheath 90, the residual limb 14 might "tack up" against the inner surface 64 and form a seal which might prevent even application of the vacuum to the cavity 62. The sheath 90 may also be used to assist the amputee into a smooth and easy fitting into the inner socket 60. The sheath 90 is preferably made of thin knitted nylon.

The hypobarically-controlled artificial limb 50 may also include a nonfoamed, nonporous polyurethane liner 92 receiving the residual limb 14 and disposed between the sheath 90 and the residual limb 14. The liner 92 provides a total-contact hypobaric suction, equal weight distribution socket liner. The liner 92 readily tacks up to the skin of the residual limb 14 and provides total contact with the limb 14. The liner 92 absorbs and dissipates shock, mechanical and shear forces typically associated with ambulation.

The hypobarically-controlled artificial limb 50 may also include a stretchable nylon second sleeve 94 for rolling over and covering the suspension sleeve 86 to prevent clothing from sticking to and catching the suspension sleeve 86.

Referring to FIG. 3, the polyurethane tubular sleeve 86 may be appreciated alone and in combination with the urethane liner 92 together with the optional nylon sheath 90 and second stretchable nylon sleeve 94.

More specifically, the amputee takes the stretchable nylon second sleeve 94, suitably made of a spandex-like material and rolls it up over the stump 14 to the upper portions of the residual limb suitably as the thigh of a leg 12. Next, the polyurethane sleeve 86 is also rolled upwardly over the residual limb 10. Thereafter, the liner 92 is optionally donned.

Next, the amputee may optionally utilize the nylon sheath 90 which is suitably of a non-stretching, thin, friction reducing nylon. As stated, this sheath 90 optionally may be used to assist the amputee into a smooth and easy fitting into the inner socket 60. Alternatively, the sheath 90 may be avoided and the liner 92 simply inserted into the inner socket 60 of the artificial limb 50.

Next, the amputee simply grasps the rolled over portion of the polyurethane sleeve 86 and rolls it over a substantial portion of the outer socket 52. The sleeve 86 makes an airtight seal between the residual limb 14 and the outer socket 52.

As can be appreciated, the polyurethane sleeve 86 is tacky. Consequently, the stretchable nylon second sleeve 94 may be utilized and rolled over the polyurethane sleeve 86.

The amputee then sets the regulator means 80 to cause the vacuum source 70 to apply vacuum through the vacuum valve 74 and vacuum tube 76 to the cavity 62. Enough vacuum is applied to cause the residual limb (with optional coverings) to be drawn firmly against the inner surface 64 of the inner socket 60, which is flexible. The vacuum source 70 may preferably maintain a vacuum in the range of 0 to 25 inches of mercury (ideally fifteen to twenty inches).

It will be seen that the vacuum within the inner socket 60 will cause the hypobarically-controlled artificial limb 50 to be suspended from the residual limb 14. The vacuum will lock the residual limb 14 into the inner socket 60 without causing swelling of the residual limb into the socket, because of the total contact of the residual limb 14 with the inner socket 60. That is, there is no open chamber between the residual limb 14 and the inner socket 60 which would draw on the residual limb.

As the volume of the residual limb 14 decreases during the day due to weight-bearing pressures, the regulator means 70 may appropriately adjust the vacuum source 70 to draw the residual limb 14 more firmly against the inner socket 60 and thus compensate for the loss of residual limb volume. The vacuum may also partially oppose the loss of fluids from the residual limb caused by weight-bearing pressures.

A second embodiment of the hypobarically-controlled artificial limb 50 is shown in FIGS. 5 and 6. The second embodiment of the hypobarically-controlled artificial limb 50 is as described above, with the exception that the inner socket 60A is compressible as well as being flexible. Instead of a vacuum source, the second embodiment has a positive air pressure source 100, which may preferably be a motor-driven pump 102. The regulator means 80, which may be a digital computer 82, controls the positive air pressure source 100. The regulator means and positive air pressure source 100 are connected to a power source 83, which may be a battery. A positive pressure valve 104 connects the space 58 to the positive air pressure source 100, for compressing the inner socket 60A as the volume of the residual limb decreases.

It will be seen that as the volume of the residual limb 14 decreases during the day due to weight-bearing pressures, the regulator means 80 may control the positive air pressure source 100 to cause air pressure to compress the inner socket 60A to compensate for the decreased volume of the residual limb, as shown in FIG. 6.

A third embodiment of the hypobarically-controlled artificial limb 50 is shown in FIG. 7. The third embodiment is a combination of the first and second embodiments described above.

The mechanical motor-driven pump 72 may act as both the vacuum source 70 and the positive air pressure source 100. The regulator means 80, vacuum source 70 and positive air pressure source 100 are connected to a power source 83, which may be a battery.

The vacuum source 70, under control of the regulator means 80, will compensate for reduced residual limb volume up to a certain point. From that point on, the regulator means 80 will cause the positive air pressure source 100 to further compensate for reduced residual limb volume as described above. The third embodiment thus uses both vacuum and positive air pressure working together to lock the residual limb 14 into the inner socket 60 and reduce socket volume to compensate for fluid loss in the residual limb 14. The exact point at which the changeover is made between vacuum compensation and positive air pressure compensation is controlled by the regulator means 80, which as described may be a digital computer appropriately programmed for the socket environment.

A fourth embodiment of the hypobarically-controlled artificial limb 50 is shown in FIG. 8. The fourth embodiment is like the first embodiment, but includes two vacuum valves: a first vacuum valve 106 and a second vacuum valve 110, both connected to the vacuum source 70. The first vacuum valve 106 connects the vacuum source 70 to the space 58. The space 58 contains a semi-compressible material 108, such as polystyrene beads, as disclosed in U.S. Pat. No. 4,828,325, herein incorporated by reference.

To don the artificial limb 50, the amputee proceeds as described above. After inserting the residual limb 14 (with optional coverings) into the inner socket 60B, which is both compressible and expandable, and rolling the suspension sleeve 86 over the outer socket 52, the amputee activates the regulator means 80, causing the vacuum source 70 to apply a vacuum to the space 58. This causes the material 108 to lock mechanically together into a rigid mass, conforming to the shape of the residual limb 14. The inner socket 60B may expand slightly under the weight of the residual limb 14 and under the influence of vacuum.

It will be seen that the semi-compressible molding material 108 can be molded to the contours of the residual limb 14 without using a custom-building process to produce a custom socket. The outer socket 52 may appropriately occur in standard sizes, such as small, medium, and large. The inner socket 60B may also occur in standard sizes such as small, medium, and large. Adaptation of the inner socket 60B to the contours of the residual limb 14 occurs through solidifying the material 108 under the influence of vacuum.

The second vacuum valve 110 connects the vacuum source 70 to the cavity 62 as previously described, for locking the residual limb 14 into the inner socket 60B.

The fourth embodiment may also include a positive air pressure source 100 as previously described, to adjust the size of the inner socket 60B to compensate for decreased residual limb volume.

The fourth embodiment may also include a thin sheath 90, liner 92, and second sleeve 94, as previously described.

The positive air pressure source 100 may also be used for shock absorption and a dynamic response in the ankle and foot sections of the artificial limb 50, by means of a connection 120.

Figure 10:
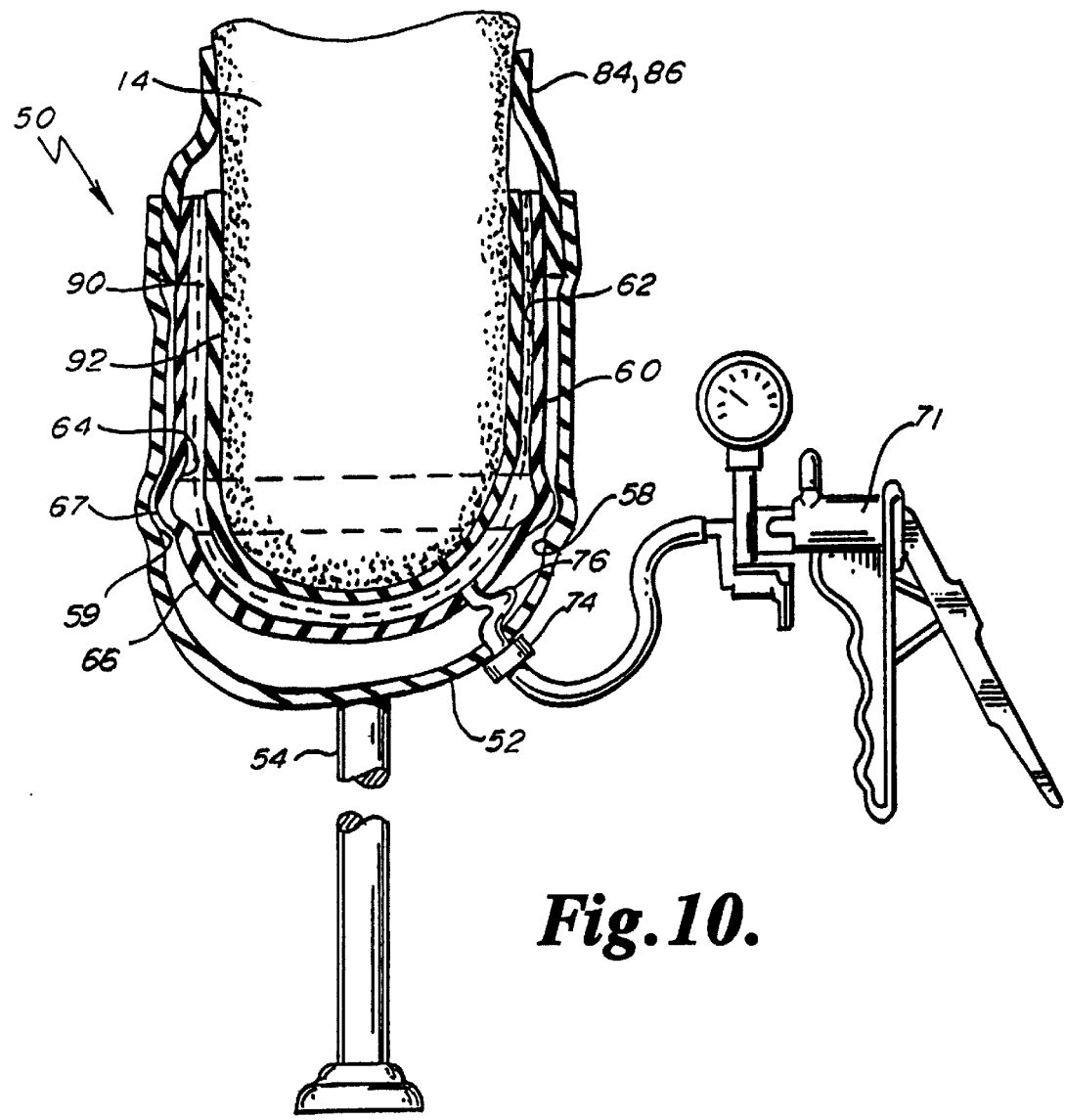
FIG. 10 is a cross-section of the artificial limb showing a fifth embodiment of the artificial limb.

A fifth embodiment of the hypobarically-controlled artificial limb 50 is shown in FIG. 10. This embodiment is the same as the first embodiment shown in FIG. 4, with some changes. First, vacuum source 71 may be a hand-operated vacuum pump 71 which may remove air from the cavity 62 down to approximately 15–25 inches of mercury. A suitable hand-operated vacuum pump is marketed under the trademark MITY VAC II® by Neward Enterprises, Inc. of Cucamonga, Calif.

The fifth embodiment also includes the seal means 84 which preferably consists of a non-foamed, nonporous polyurethane suspension sleeve 86 for rolling over and covering a portion of the residual limb 14. A portion of the seal means 86 is adapted to be disposed between the outer socket 52 and the inner socket 60. The sleeve may be made of any of a variety of air-impervious elastomers.

The fifth embodiment, shown in FIG. 10 also includes a mechanical interlock 67, 59 for interlocking the inner socket 62 with the outer socket 52. Preferably, the mechanical interlock consists of a first detent 67 in the inner socket 62 and a second detent 59 in the outer socket 52. The first detent 67 engages the second detent 59 to lock the inner socket 60 into the outer socket 52.

Figure 12:
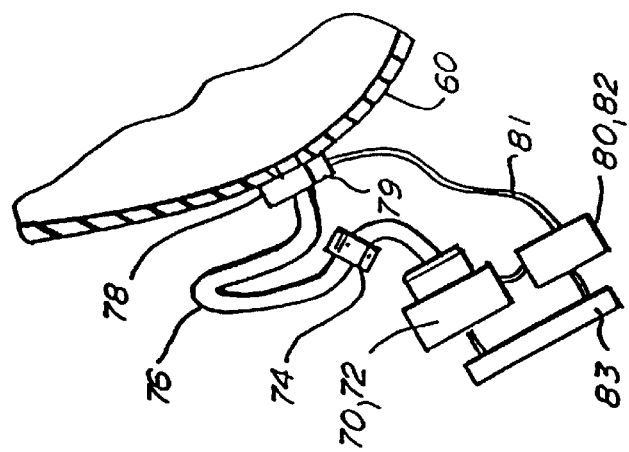
FIG. 12 is a detailed view of the vacuum mechanism in FIG. 11.
Figure 11:
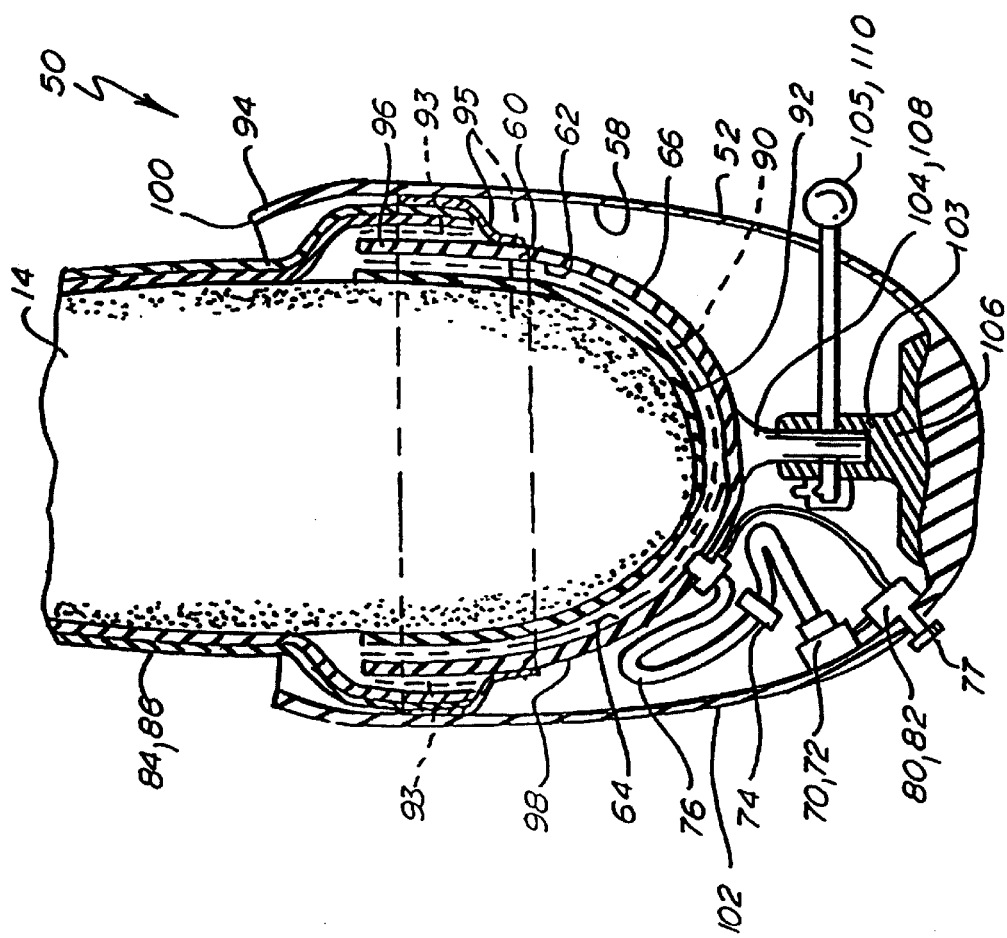
FIG. 11 is a cross-section of the artificial limb showing a sixth embodiment of the artificial limb.

A sixth embodiment of the hypobarically-controlled artificial limb of the present invention is shown in FIGS. 11 and 12. The sixth embodiment is like the first embodiment shown in FIG. 4, with some changes.

First, the inner socket is specifically intended to be removably from the outer socket. To provide a positive mechanical connection between the inner socket and outer socket and yet allow the inner socket to be easily removed, the sixth embodiment includes a mechanical interlock 103 engaging the inner socket 60 and the outer socket 52. Preferably, the mechanical interlock may be an extension 104 which is attached to the inner socket 60 and a docking device 106 attached to the outer socket 52 and receiving the extension 104, and a locking mechanism 105 engaging the extension 104 and the docking device 106.

The extension may be any sort of protrusion from the inner socket, such as a bulge or tab. Preferably, the extension 104 comprises a shuttle pin 108.

The locking mechanism may be any sort of member which engages both the extension 104 and the docking device 106, such as a screw, wire, or pin. Preferably, the locking mechanism 105 comprises a second pin 110 which extends outside the outer socket 52 as to be accessible.

Second, the sixth embodiment includes two thin sheaths, rather than one. A first inner sheath 90 may preferably be disposed between the residual limb 14 and the inner surface 64 of the inner socket 60. As vacuum is applied to the cavity 62, the inner sheath 90 will allow the vacuum to be evenly applied throughout the cavity 62. Without the inner sheath 90, the residual limb 14 might "tack up" against the inner surface 64 and form a seal which might prevent even application of the vacuum to the cavity 62. The inner sheath 90 may also be used to assist the amputee into a smooth and easy fitting into the inner socket 60.

An outer sheath 93 is preferably disposed between the suspension sleeve 86 and the inner socket 60, thereby preventing the suspension sleeve from tacking to the inner socket 60. Such tacking would cause friction between the inner socket 60 and the sleeve 86 which would cause the sleeve to wear out. Such tacking might also cause restrictions in the movement of the residual limb. The outer sheath 93 also protects the suspension sleeve 86 from being damaged by friction with the inner socket 60.

The sixth embodiment also preferably includes an adhesive pressure tape 95 adapted to cover the outer sheath 93, suspension sleeve 86, and the second sleeve 94 and sealing the outer sheath 93, suspension sleeve 86, and the second sleeve 94 to the inner socket 60. The tape 95 locks all of these layers to the inner socket so that they do not come loose during movement.

In the sixth embodiment, the suspension sleeve 86 goes between the inner socket 60 and the outer socket 52, so that the sleeve 86 is protected from damage.

In the sixth embodiment, the inner socket 60 has a rigid lower portion 98 and a substantially flexible upper portion 96. The rigid lower portion assists in weight-bearing while the substantially flexible upper portion allows for movement of the residual limb 14. As the knee is bent from fully straight to fully flexed, the width of the knee changes rather significantly and in a hard, non-flexible socket brim, there can be excessive pressure on the residual limb 14. The substantially flexible upper portion 96 makes the artificial limb 50 more comfortable and more adaptive to these changes. For the same reason, the outer socket 52 has a rigid lower portion 102 and a substantially flexible upper portion 100.

Preferably, the top edge of the inner socket 60 is below the top edge of the outer socket 52 so that the sleeve 86 is protected from impact. Preferably, the top edge of the inner socket 60 may be 3/16 inch below the top edge of the outer socket 52.

The sixth embodiment includes extensive modifications to the vacuum system.

First, a vacuum fitting 78 has been added to the inner socket 60 to attach the vacuum tube 76. The vacuum fitting 78 allows the attachment of a vacuum sensor 79 adapted to sense the amount of vacuum in the cavity 62 and a sensor lead 81 is attached to the sensor 79 connecting the sensor 79 to the regulator means 80, thus conveying the sensed vacuum to the regulator means 80.

A vacuum valve 74 is placed between the cavity 62 and the vacuum source 70 to maintain vacuum in the cavity 62. Typically, the vacuum valve 74 is a one-way valve or non-return valve.

In the sixth embodiment, the vacuum source 70, vacuum tube 76, vacuum valve 74, regulator means 80, and power source 83 are all attached to the outer socket 52 in the space 58 between the outer socket 52 and inner socket 60. In this way, these delicate components are protected against being damaged by impact. Because of the placement of the regulator means 80 within the outer socket 52, a vacuum control 77 is provided extending outside the outer socket 52 to allow manual control of the regulator means 80.

The amputee dons the sixth embodiment in a manner similar to that earlier described, with some modifications. First, the outer sheath 93 is put on the residual limb 14 after rolling the suspension sleeve 86 upward over the residual limb and before donning the liner 92. After donning the inner sheath 90 over the liner 92, the amputee inserts the residual limb 14 into the inner socket 60. Next, the outer sheath 93, suspension sleeve 86, and second sleeve 94 are rolled down over the inner socket 60, and the adhesive pressure tape 95 is applied. Next, the wearer sets the regulator means 80 to an appropriate vacuum level by means of the vacuum control 77, and connects the vacuum tube 76 to the vacuum fitting 78. The inner socket 60 is then placed within the outer socket 52 so that the shuttle pin 108 engages the docking device 106 and the locking pin 110 is set to engage the shuttle pin 108 and the docking device 106, providing a positive mechanical interlock.

A seventh embodiment of the hypobarically-controlled artificial limb of the present invention is shown in FIG. 13.

The seventh embodiment is similar to the sixth embodiment, with some changes.

First, the mechanical interlock 103 does not engage the inner socket 60. Instead, the mechanical interlock engages the outer socket 52 and the suspension sleeve 86. To accomplish this, the suspension sleeve 86 covers the entire inner socket 60, and the suspension sleeve 86 has the extension 104 or shuttle pin 108 embedded in the suspension sleeve at the distal end of the suspension sleeve, as shown in FIG. 14. Preferably, the extension 104 has a portion 104A embedded in the suspension sleeve. This portion 104A may be a disk or umbrella 104A. The extension 104 then engages the docking device 106 as previously described.

Second, the suspension sleeve 86 is modified to support the additional weight imposed on the suspension sleeve 86 due to the outer socket 52 and artificial limb. In particular, the suspension sleeve 86 is fabricated from a material which allows circumferential expansion but resists longitudinal stretching under the weight of the artificial limb. Such a material is described in U.S. Pat. No. 5,571,208, herein incorporated by reference.

The sleeve 86 preferably contains fabric threads which may be oriented circumferentially around the sleeve. The threads preferably are comprised of double-knit polyurethane. The threads may also include nylon. The threads permit the sleeve 86 to expand circumferentially so that the sleeve may be slipped onto the residual limb 14 and so that the lower portion may be slipped over the inner socket 52. The threads are preferably connected together with crosslinks, which also may be preferably comprised of polyurethane. The cross-links and threads form a matrix which allows circumferential expansion but resists longitudinal stretching under the weight of the artificial limb. By example, the sleeve 86 may have a 4-to-1 ratio of circumferential stretch relative to longitudinal stretch.

The sleeve 86 may have a portion above the inner socket 52 which is manufactured of material which allows both vertical and horizontal stretching, to increase flexibility.

Figure 15:
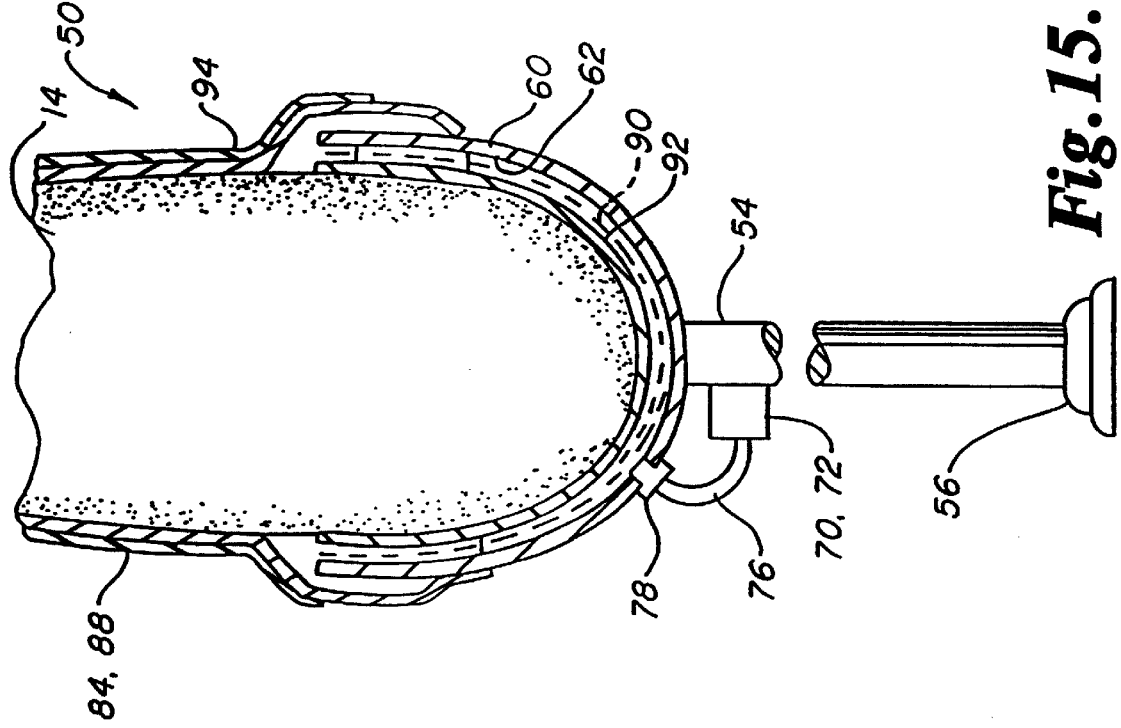
FIG. 15 is a cross-section of the artificial limb showing an eighth embodiment of the artificial limb.
Figure 17:
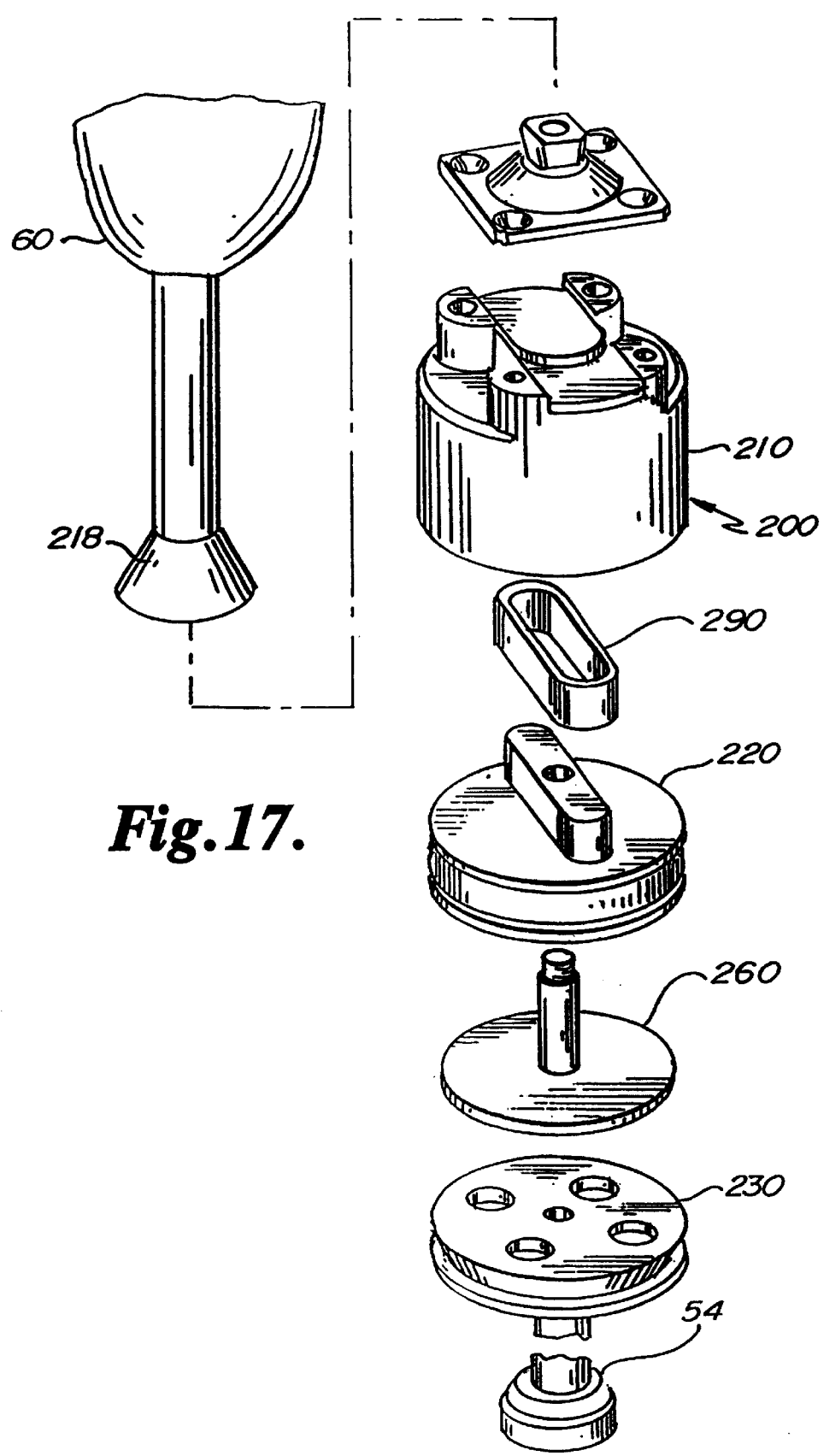
FIG. 17 is an exploded perspective view of a first embodiment of a weight-activated vacuum pump and shock absorber.
Figure 18:
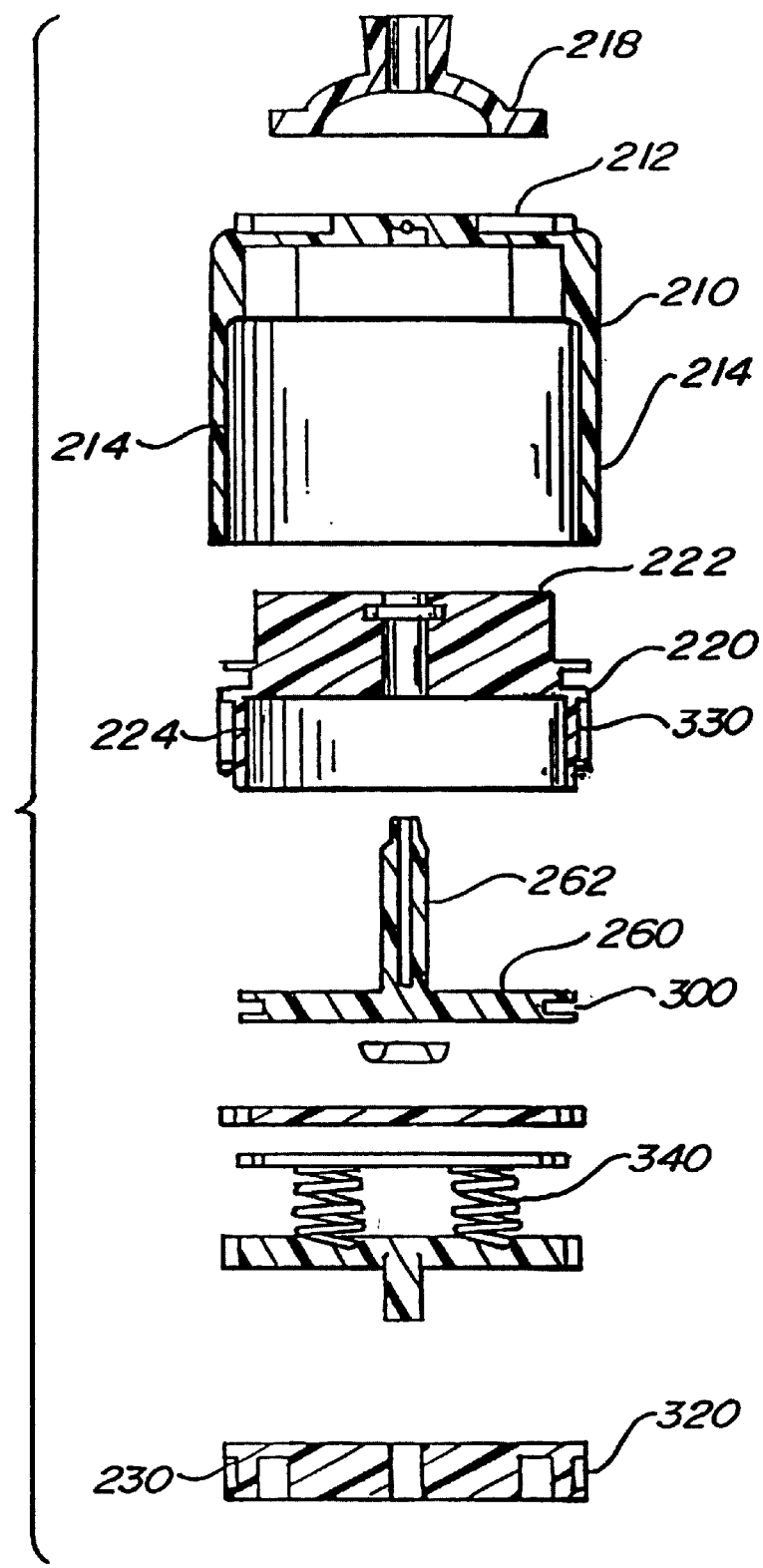
FIG. 18 is a diagrammatic exploded view of a first embodiment of a weight-activated vacuum pump and shock absorber.
Figure 19A:
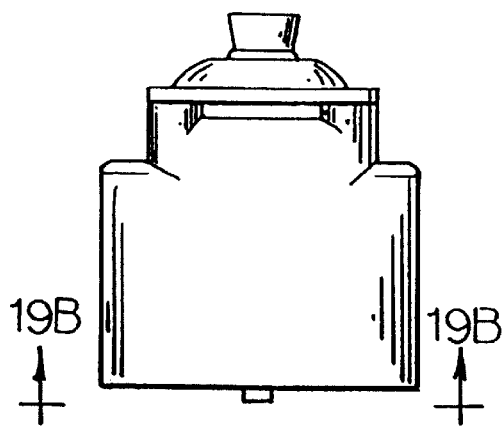
FIG. 19A is a side elevational view of a first embodiment of a weight-activated vacuum pump and shock absorber.
Figure 19B:
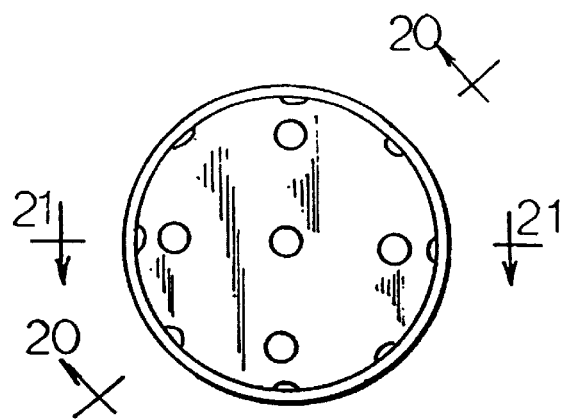
FIG. 19B is a cross-section along the lines 19B of FIG. 19A.
Figure 20:
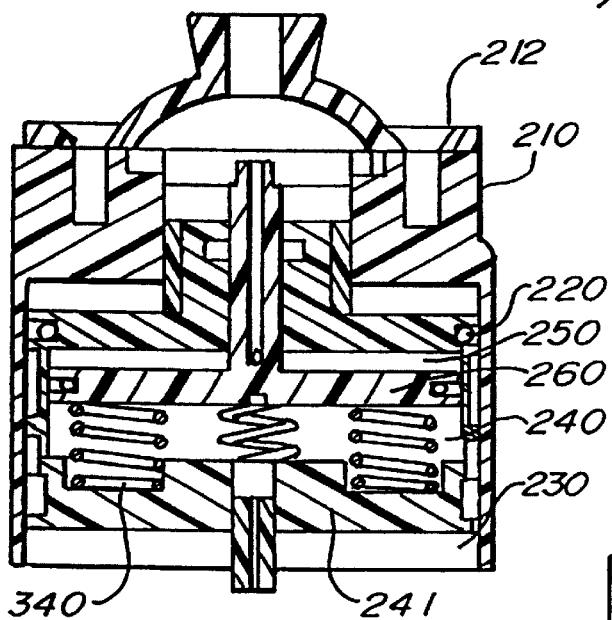
FIG. 20 is a cross-section along the lines 20 of FIG. 19B.
Figure 21:
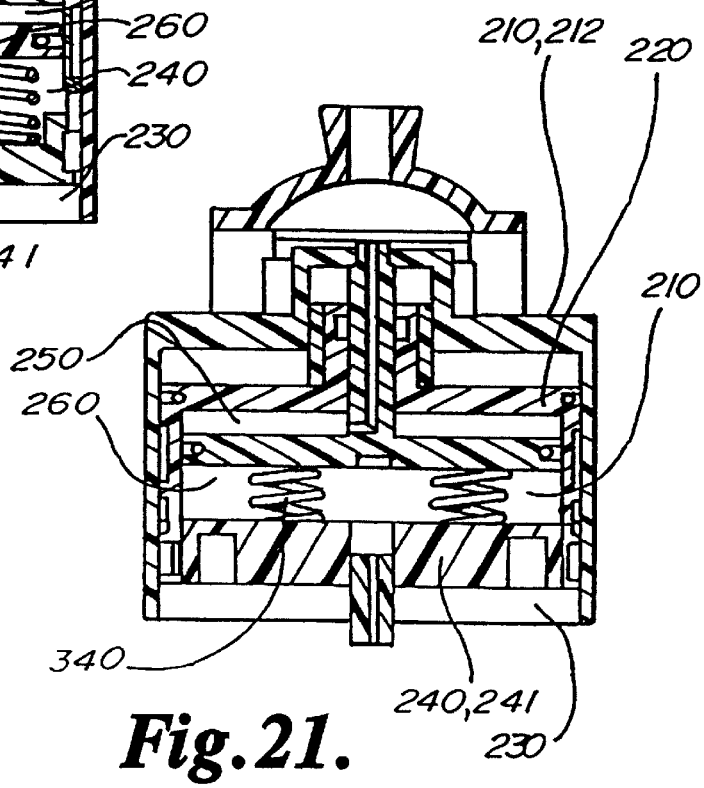
FIG. 21 is a cross-section along the lines 21 of FIG. 19B.

An eighth embodiment of the hypobarically-controlled artificial limb of the present invention is shown in FIG. 15.

Unlike earlier embodiments, the artificial limb 50 of the eighth embodiment has only a single socket 60 rather than inner and outer sockets and is thus considerably simpler.

The socket 60 has a volume and shape to receive a substantial portion of the residual limb 14 with a cavity 62 therebetween.

A nonfoamed, nonporous polyurethane liner 92 is preferably adapted to receive the residual limb 14 and to be disposed between the residual limb 14 and the socket 60.

A vacuum source 70 is connected to the cavity 62 by a vacuum valve 78, thereby drawing the residual limb 14 into firm contact with the socket 60.

A seal means 84 makes a seal between the residual limb 14 and the socket 60 to minimize air leakage into the cavity 62. It has been found that it is impossible to make a perfect seal, with the result that air leakage can occur at rates up to 30 cc per minute. As air leaks into the cavity 62, it is necessary to activate the vacuum source 70 to restore vacuum in the cavity. Furthermore, it has been found that when the vacuum in the cavity is about 5 inches of mercury, the residual limb may lose up to 6 to 15% of its volume during the day, whereas if the vacuum in the cavity is 15–25 inches of mercury, the residual limb loses only about 1% of its volume during the day.

Figure 16:
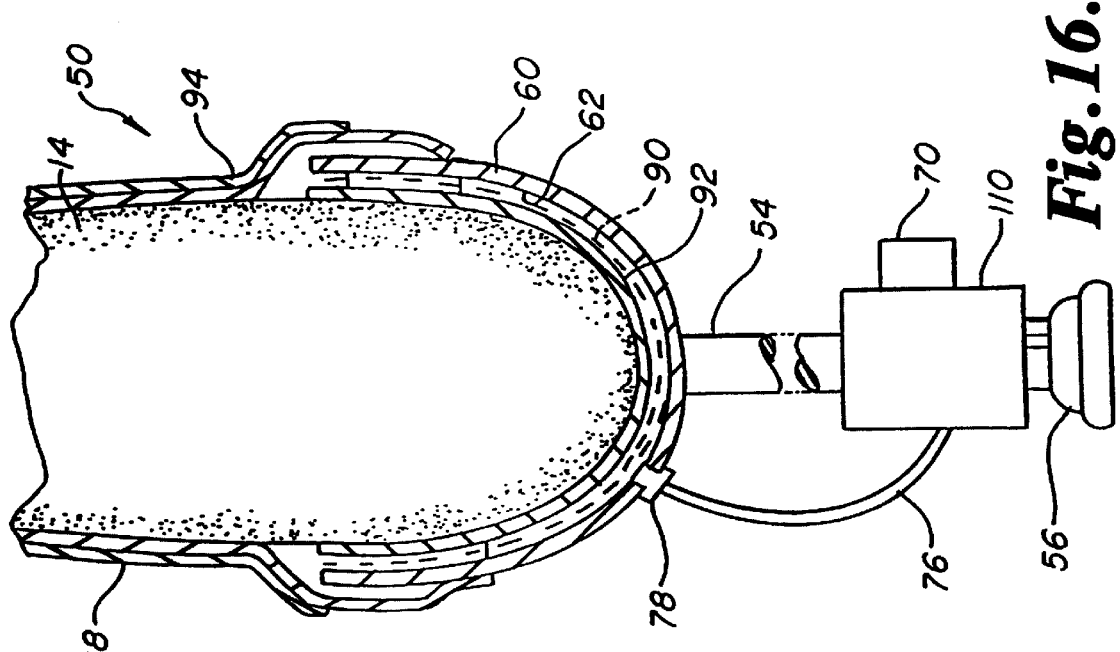
FIG. 16 is a cross-section of the artificial limb showing a ninth embodiment of the artificial limb.

To minimize the time that the vacuum source, such as a vacuum pump 72, needs to run to maintain vacuum in the cavity, a ninth embodiment of the artificial limb 50 is shown in FIG. 16. The ninth embodiment is the same as the eighth embodiment, but a vacuum reservoir 110 is added between the vacuum source 70 and the vacuum valve 78. The vacuum reservoir 110 has a volume substantially larger than the cavity 62. Suitably, the vacuum reservoir may have a volume of 2 gallons or 9000 cc while the volume of the cavity 62 may be only about 100 cc or even less.

It will be seen that as air leaks into the cavity 62, the air will be pulled into the vacuum reservoir 110, thereby maintaining the vacuum in the cavity 62.

When the vacuum in the reservoir 110 reaches a certain minimum threshold, the vacuum source 70 may be activated to restore vacuum to the vacuum reservoir 110. The vacuum source 70 may be activated either manually or by a regulator means (not shown).

The artificial limb 50 typically includes a shin or pylon 54 and a foot 56, as shown in FIG. 3. Preferably, the vacuum reservoir 110 is attached to the shin 54 between the socket 60 and the foot 56. However, the vacuum reservoir may also be carried separately, as for example in a backpack. Depending on the placement of the vacuum reservoir 110, a vacuum tube 76 may be necessary to connect the vacuum reservoir 110 to the vacuum valve 78.

If the volume of the vacuum reservoir 110 is about 9000 cc and air leaks into the cavity 62 at about 75 cc per minute, it will be seen that the intervals between activation of the vacuum source 70 can be up to about 120 minutes.

The artificial limb 50 of the eighth and ninth embodiments may preferably further comprise the following.

An inner sheath 90 may be adapted to be disposed between the liner 92 and the socket, to ensure even distribution of vacuum in the cavity 62, as earlier described. Preferably, the inner sheath 90 may be thin knitted nylon. The sheath 90 may also be affixed to the outside of the liner 92.

The seal means 84 is preferably a nonfoamed, nonporous polyurethane suspension sleeve 86 for rolling over and covering the socket 60 and a portion of the artificial limb 14, as earlier described.

A stretchable nylon second sleeve 94 for rolling over and covering the suspension sleeve 86 may be added to prevent clothing from sticking to and catching on the suspension sleeve 86, as earlier described.

The vacuum source 70 is preferably a motor or mechanical driven vacuum pump 72, as earlier described. A vacuum tube 76 may be necessary to connect the vacuum pump 72 to the vacuum valve 78, depending on the placement of the vacuum pump 72.

A first embodiment of a vacuum pump and shock absorber for an artificial limb is shown in FIGS. 17–25.

The vacuum pump and shock absorber 200 in one aspect comprises a housing 210 fixedly attached to the socket 60 and having a housing top wall 212 and housing side walls 214.

A cylinder 220 reciprocates within the housing 210 and sealingly engages the housing side walls 214. The cylinder 220 has a cylinder top wall 222 and cylinder side walls 224.

The cylinder 220 is fixedly attached to a cap 230 and the cap 230 is fixedly attached to the pylon 54.

A piston 260 is fixedly attached to the housing 210 and reciprocates within the cylinder 220. Preferably, the piston 260 screws to the housing 210.

The cylinder top wall 222, cylinder side walls 224, and piston 260 cooperate to form a first chamber 240.

The cylinder top wall 222, the housing top wall 212, and the housing side walls 214 cooperate to form a second chamber 250.

The piston 260, cylinder side walls 224 and cap 230 cooperate to form a third chamber 241.

A first valve means 270 connects the first chamber 240 and the second chamber 250 to the cavity 62 and to the atmosphere. A second valve means 280 connects the second chamber 250 and the first chamber 240 to the cavity 62 and to the atmosphere. An intake/exhaust port 272 is placed between the first valve means 270 and the first chamber 240. An intake port 274 connects the second chamber 250 to the first valve means 270. An exhaust port 284 connects the second chamber 250 to the second valve means 280.

Preferably, the first valve means 270 may be a three-way valve 272 and the second valve means 280 is a second three-way valve 282.

The weight-activated vacuum pump 200 also preferably comprises an anti-rotation collar 290 between the cylinder 220 and the housing 210.

A first seal 300 is placed between the piston 260 and the cylinder side walls 224 and a second seal 310 is placed between the cylinder side walls 224 and the housing side walls 214. Preferably a first bushing 320 is placed between the cap 230 and the housing side walls 214 and a second bushing 330 is placed between the cylinder side walls 224 and the housing side walls 214.

Preferably, the housing top wall 210 has a hollow core 216 and the piston 260 has a stem 262 slidingly engaging the hollow core 216. Most preferably, the intake/exhaust port 272 traverses the stem 262.

The weight-actuated vacuum pump and shock absorber 200 also preferably comprises a spring 340 biasing the cylinder 220 toward the housing top wall 212. Alternatively, compressed air in the third chamber 241 biases the cylinder 220 toward the housing top wall 212. An adjustment valve 350 may be provided to vary the pressure of compressed air between the piston 260 and the cap 230.

Operation of the first embodiment of the weight-actuated vacuum pump and shock absorber 200 may now be described.

Figure 22:
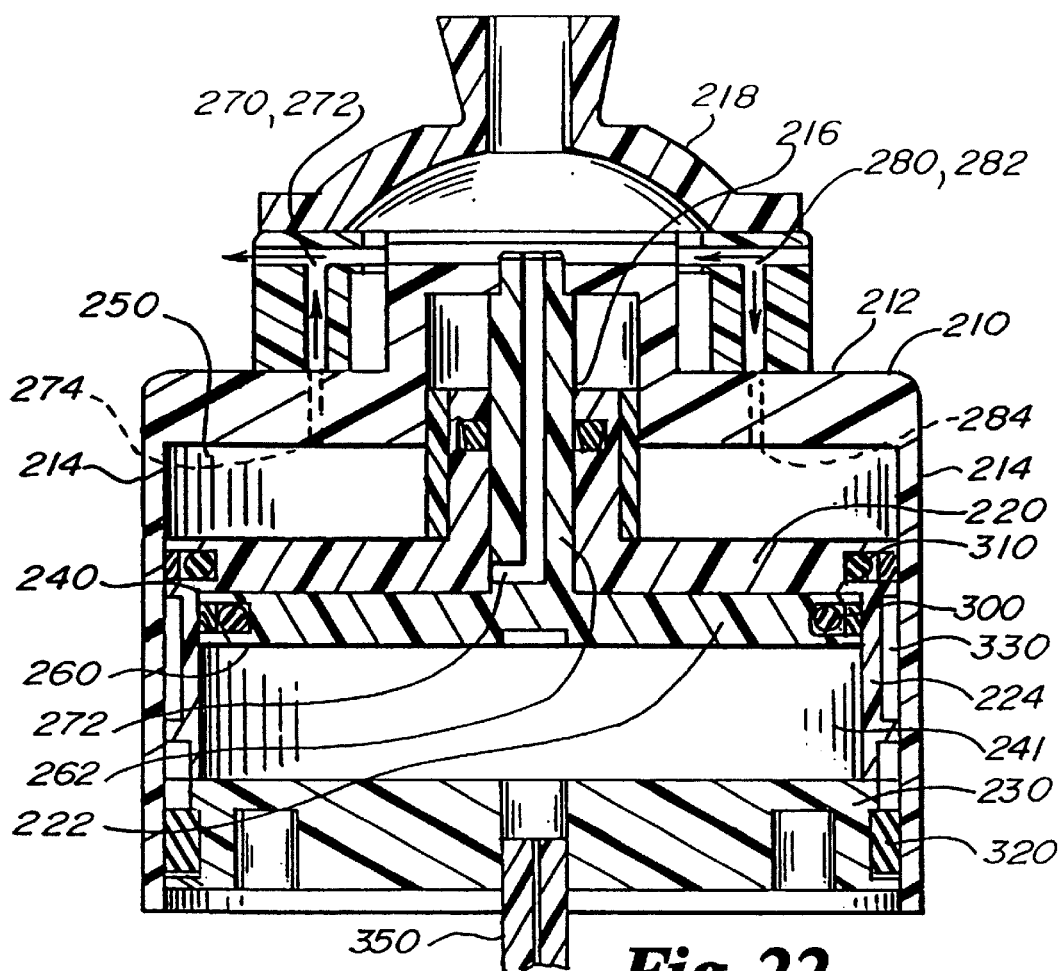
FIG. 22 is a detailed cross-section of a first embodiment of a weight-activated vacuum pump and shock absorber in the unweighted state.
Figure 26:
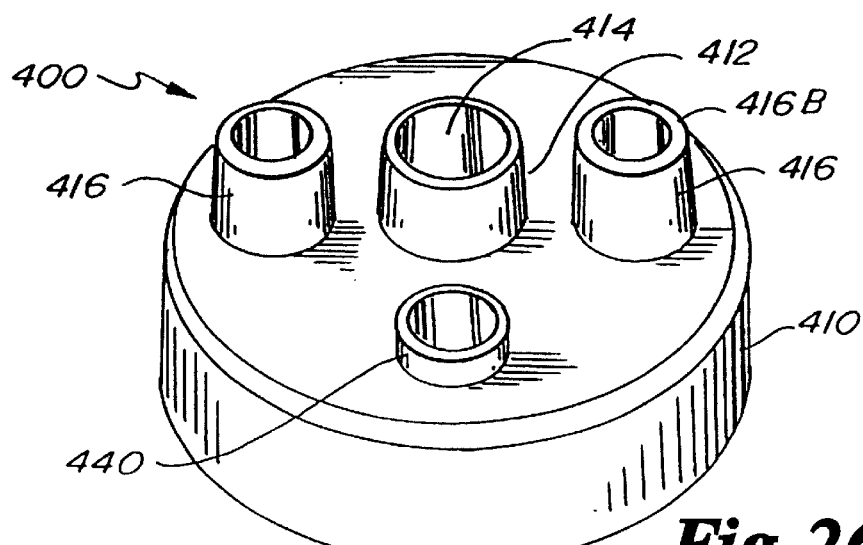
FIG. 26 is a top perspective view of a second embodiment of a weight-actuated vacuum pump and shock absorber, with some structure removed.

FIG. 22 shows the pump 200 in a state where the wearer is not applying any body weight to the pylon 54, as when sitting down or at the completion of the swing phase of walking. As can be seen, the piston 260 abuts the cylinder top wall 220, forced there either by compressed air in the third chamber 241 or by the spring 340. The housing 210, which is attached to the piston 260 is at the top of its travel, with the second chamber 250 expanded to its maximum volume. The first valve means 270 is closed, sealing off the cavity 62 from the pump 200. The second valve means 280 is open to atmosphere.

FIG. 23 shows what happens as the wearer begins to apply body weight to the pylon 54. The housing 210, attached to the socket 60 by connector 218, is forced downward, carrying the piston 260 with it. The housing side walls 214 slide along the cylinder side walls 224. Because the cylinder 220 is fixed to the pylon 54 and does not move, this motion of the housing 210 decreases the volume of the second chamber 250, causing air to be forced out of the second chamber 250 through the second valve means 280, as shown by the dark arrow. Simultaneously, the piston 260 moving downwardly within the first chamber 240 draws air from the cavity 62 through the first valve means 270, which has connected the intake/exhaust port 272 to the cavity 62, producing a vacuum in the cavity 62, as shown by the light arrows. The motion of the piston 260 will also compress air in the third chamber 241 between the piston 260 and the cap 230, providing a shock absorbing function.

Figure 24:
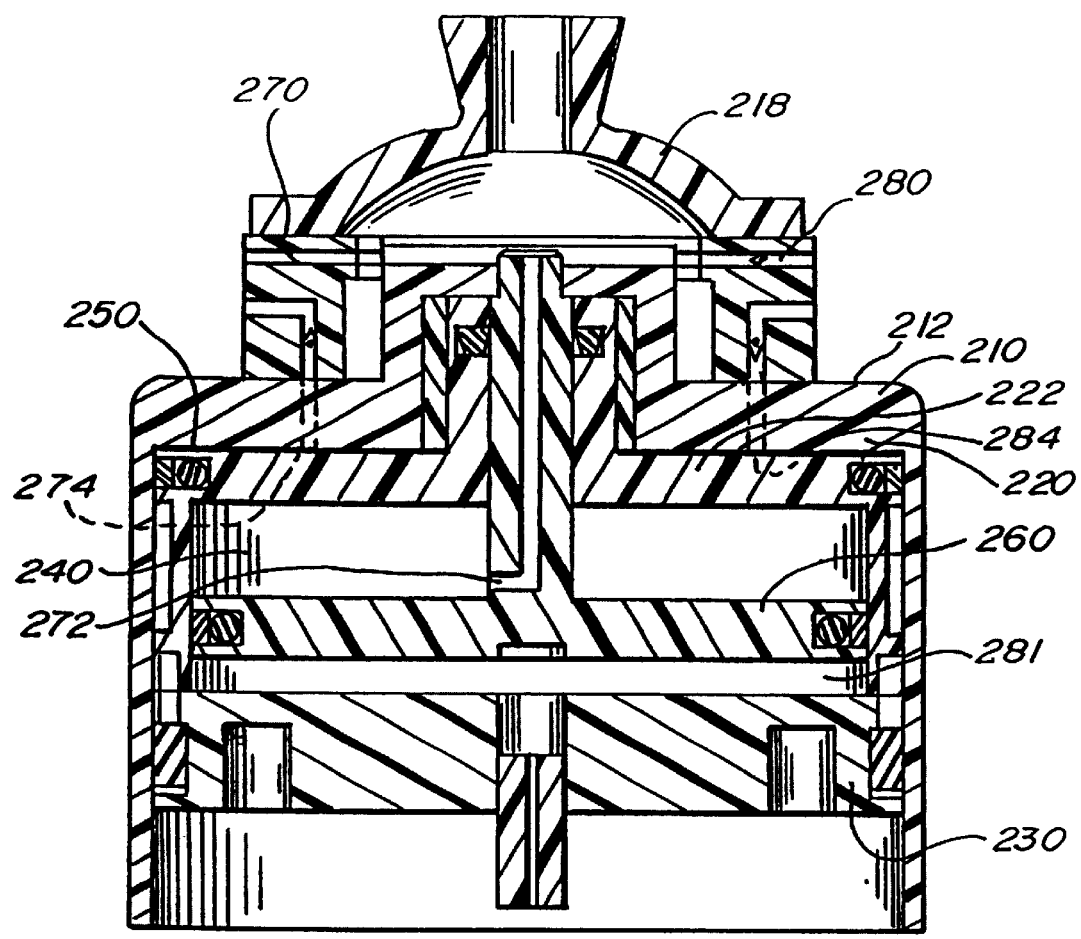
FIG. 24 is the same as FIG. 23, with the wearer's weight fully applied to the pylon of the artificial limb.
Figure 28:
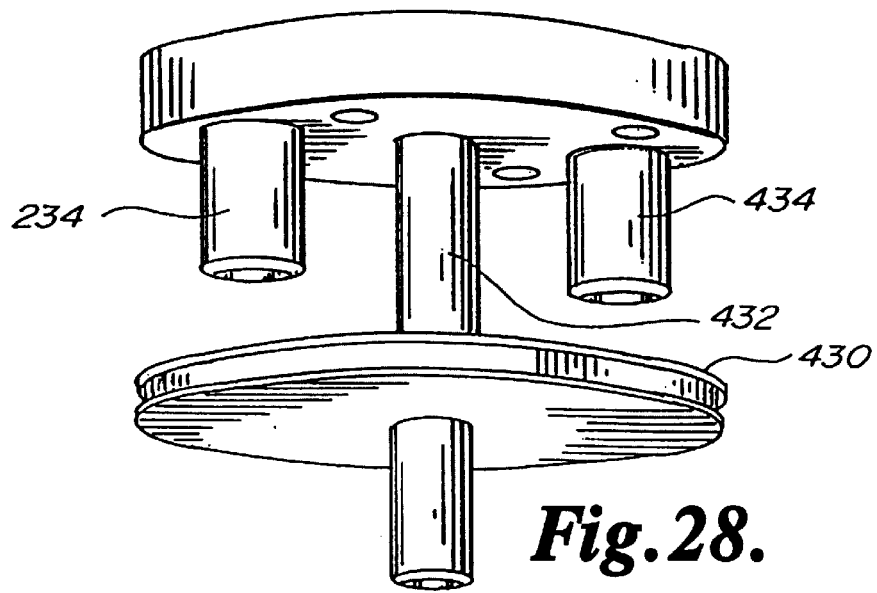
FIG. 28 is a perspective view of some internal structure of a second embodiment of a weight-actuated vacuum pump and shock absorber.

FIG. 24 shows the state where the wearer has placed all of his body weight on the pylon 54, and the housing 210 and piston 260 are at their maximum travel relative to the cylinder 220. The first chamber 240 is at its maximum volume and the second chamber 250 is at its minimum volume. The first valve means 270 has been switched to connect the second chamber 250 to the cavity 62.

Figure 25:
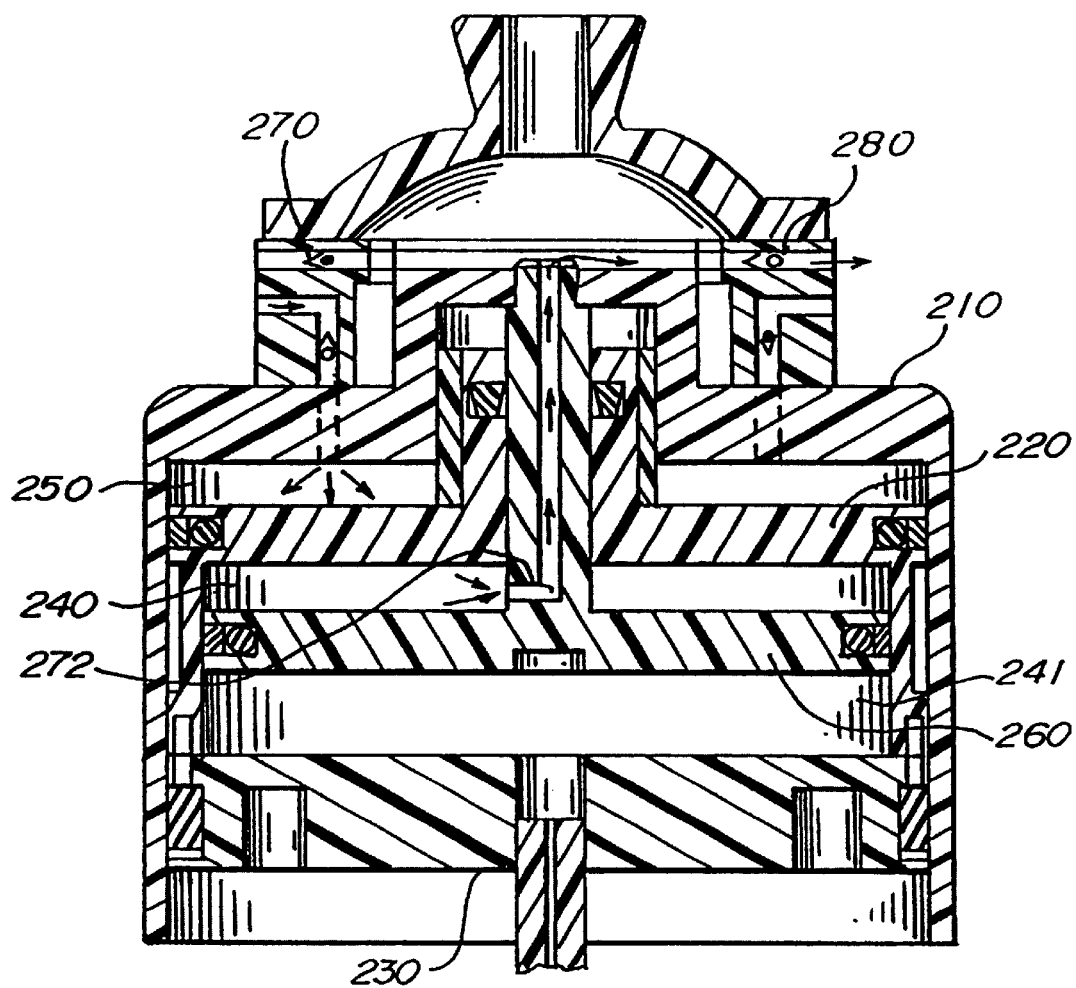
FIG. 25 is the same as FIG. 23, with the wearer's weight being removed from the pylon of the artificial limb.
Figure 29A:
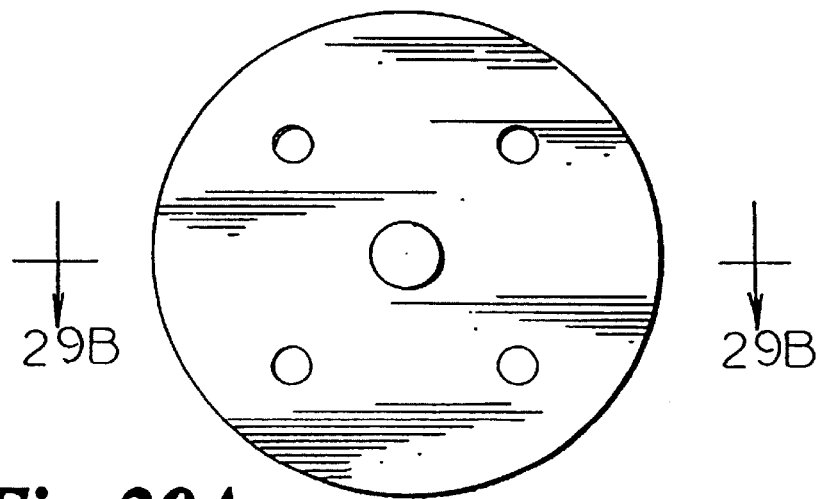
FIG. 29A is a top plan view of a second embodiment of a weight-actuated vacuum pump and shock absorber.
Figure 29B:
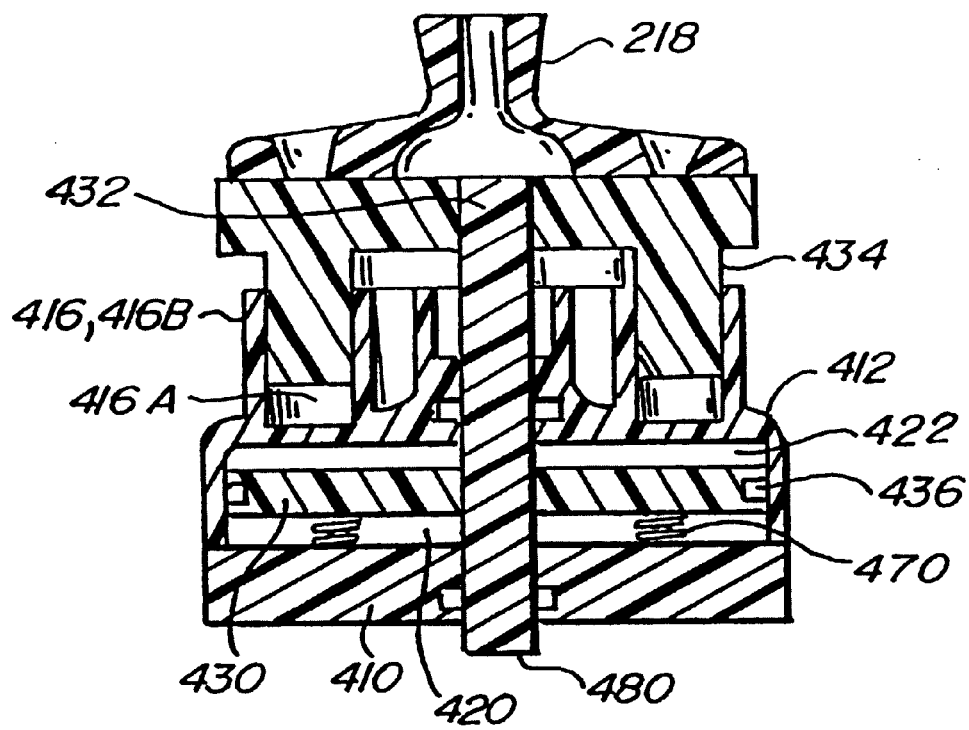
FIG. 29B is a cross-section along the lines 29B of FIG. 29A.

FIG. 25 shows what happens when the wearer removes his body weight from the pylon 54, as in the beginning of the swing phase of ambulation. Under the influence of compressed air in the third chamber 241 or of the spring 340, the housing 210 and piston 260 are forced upwardly, causing air in the first chamber 240 to be forced out of the first chamber 240 through the intake/exhaust port 272 and second valve means 280 to atmosphere, as shown by the dark arrows. Simultaneously, the motion of the housing 210 increases the volume of the second chamber 250, causing air to be drawn into the second chamber 250 from the cavity 62 through the first valve means 270, again increasing the amount of vacuum in the cavity 62, as shown by the light arrows.

Throughout operation of the pump 200, the anti-rotation collar 290 prevents the cylinder 220 from rotating within the housing 210.

A second embodiment of a weight-actuated vacuum pump and shock absorber is shown in FIGS. 26–29. Unlike the first embodiment, which is a double-action pump, the second embodiment is a single-action pump.

The weight-actuated vacuum pump 400 comprises a cylinder 410 attached to the pylon 54 and having a first chamber 420 therein. A piston 430 reciprocates within the first chamber 420. The piston 430 extends outside the cylinder 410 and is fixedly attached to the socket 62 as by connector 218. Preferably, the cylinder 410 has a top wall 412 with an aperture 414 therethrough, and the piston 430 has a stem 432 slidingly engaging the aperture 414.

The piston has a seal 436 along its periphery separating the first chamber 420 from a second chamber 422 between the piston 430 and the cylinder top wall 412.

The cylinder top wall 412 may preferably further comprise a plurality of tubes 416 with a closed end 416A and open end 416B, the open end 416B facing the socket 60. The stem 432 may have a plurality of projections 434 slidingly engaging said tubes 416. The projections 434 sliding within the tubes 416 prevent the stem 432 from rotating within the aperture 414.

An intake/exhaust port 440 is connected to the first chamber 420. A first one-way valve 450 connects the intake/exhaust port 440 to the cavity 62. A second one-way valve 460 connects the intake/exhaust port to atmosphere.

Optionally, a spring 470 biases the piston 430 toward the socket 60. Alternatively, compressed air in the first chamber 420 biases the piston 430 toward the socket 60. An adjustment valve 480 may be used to vary the pressure of compressed air in the first chamber 420.

Applicant has found that the pump may generate up to 22 inches mercury of vacuum in the cavity as the wearer takes seven steps.

Operation of the second embodiment may now be described.

As the wearer brings his body weight to bear on the pylon 54, the piston 430 is forced downwardly within the cylinder 418 against compressed air or the spring 470, providing a shock-absorbing effect. At the same time, air is drawn into the second chamber 422 from the cavity 62 through the first one-way valve 450 and the intake/exhaust port 440, producing a vacuum within the cavity 62.

As the wearer removes his body weight from the pylon 54, the piston 430 is forced upwardly within the first cylinder 410 either by the spring 470 or compressed air, forcing air out of the second chamber 422 through the intake/exhaust port 440 and the second one-way valve 460 to atmosphere.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. In a hypobarically-controlled artificial limb for amputees who have a residual limb, the artificial limb having a socket with a volume and shape to receive a substantial portion of the residual limb with a cavity therebetween, a foot, and a pylon between the foot and the socket; a weight-activated vacuum pump and shock absorber apparatus attached to the pylon, said vacuum pump and shock absorber apparatus comprising:

(a) a vacuum pump activated by the wearer's body weight and adapted to pump air from the cavity to generate a vacuum therein; and (b) a shock absorber cooperating with the vacuum pump to cushion the residual limb against the wearer's body weight during ambulation.

2. The apparatus of claim 1, wherein the vacuum pump is a double-action pump.

3. The apparatus of claim 1, wherein the vacuum pump is a single-action pump.

4. The apparatus of claim 2, wherein the vacuum pump further comprises:

(a) a housing fixedly attached to the socket and having a housing top wall and housing side walls;

(b) a cylinder reciprocating within said housing and sealingly engaging said housing side walls;

(c) said cylinder having a cylinder top wall and cylinder side walls and being fixedly attached to a cap, said cap being fixedly attached to the pylon;

(d) a piston fixedly attached to said housing and reciprocating within said cylinder, said cylinder top wall, cylinder side walls and said piston cooperating to form a first chamber;

(e) said cylinder top wall, said housing top wall and said housing side walls cooperating to form a second chamber;

(f) said piston, said cylinder side walls and said cap cooperating to form a third chamber;

(g) first valve means connecting said first chamber to the cavity and to the atmosphere; and (h) second valve means connecting said second chamber to the cavity and to the atmosphere.

5. The apparatus of claim 4, wherein said second valve means is a three-way valve.

6. The apparatus of claim 4, further comprising an anti-rotation collar between said cylinder and said housing.

7. The apparatus of claim 4, wherein said piston screws to said housing.

8. The apparatus of claim 4, further comprising a first seal between said piston and said cylinder side walls and a second seal between said cylinder side walls and said housing side walls.

9. The apparatus of claim 4, further comprising a first bushing between said cap and said housing side walls and a second bushing between said cylinder side walls and said housing side walls.

10. The apparatus of claim 4, further comprising an intake/exhaust port between said first valve means and said first chamber.

11. The apparatus of claim 10, said cylinder top wall having a hollow core and said piston having a stem slidingly engaging said hollow core, and wherein said intake/exhaust port traverses said stem.

12. The apparatus of claim 4, wherein said shock absorber further comprises a spring biasing said cylinder toward said housing top wall.

13. The apparatus of claim 4, wherein said shock absorber further comprises air compressed between said piston and said cap biasing said cylinder toward said housing top wall.

14. The apparatus of claim 13, further comprising an adjustment valve adapted to vary the pressure of air between said piston and said cap.

15. The apparatus of claim 2, wherein said vacuum pump further comprises:
   (a) a cap fixedly attached to the pylon;
   (b) a cylinder fixedly attached to said cap, said cylinder having a cylinder top wall and cylinder side walls, said cylinder top wall and said cylinder sidewalls cooperating with said cap to form a first chamber;
   (c) a piston reciprocating within said first chamber;
   (d) a housing fixedly attached to the socket and to said piston, said housing having a housing top wall and housing side walls, said housing top wall and said housing side walls cooperating with said cylinder to form a second chamber, said housing side walls slidingly engaging said cylinder side walls;
   (e) an intake/exhaust port in said first chamber;
   (f) an intake port in said second chamber;
   (g) an exhaust port in said second chamber;
   (h) a three-way valve connecting said intake/exhaust port and the cavity to atmosphere;
   (i) a two-way valve connecting said intake port to the cavity; and
   (j) an exhaust valve connecting said exhaust port to the atmosphere; wherein application of the wearer's body weight to said housing moves said piston downwardly within said first chamber, causing air to be drawn out of the cavity and into said first chamber through said three-way valve and said intake/exhaust port and simultaneously forcing air out of said second chamber through said exhaust port, and wherein removal of the wearer's body weight from said housing moves said piston upwardly within said first chamber, forcing air out of said first chamber through said intake/exhaust port and said three-way valve and simultaneously drawing air out of the cavity and into said second chamber through said two-way valve.

16. The apparatus of claim 15, wherein said piston screws to said housing.

17. The apparatus of claim 15, further comprising an anti-rotation collar between said cylinder and said housing.

18. The apparatus of claim 15, further comprising a first seal between said piston and said cylinder side walls and a second seal between said cylinder side walls and said housing side walls.

19. The apparatus of claim 15, further comprising a first bushing between said cap and said housing side walls and a second bushing between said cylinder side walls and said housing side walls.

20. The apparatus of claim 15, said cylinder top wall having a hollow core and said piston having a stem slidingly engaging said hollow core.

21. The apparatus of claim 20, wherein said intake/exhaust port traverses said stem.

22. The apparatus of claim 15, said shock absorber further comprising a spring biasing said cylinder toward said housing top wall.

23. The apparatus of claim 15, said shock absorber further comprising air compressed between said piston and said cap biasing said cylinder toward said housing top wall.

24. The apparatus of claim 23, further comprising an adjustment valve adapted to vary the pressure of air between said piston and said cap.

25. The apparatus of claim 3, wherein said vacuum pump further comprises:
   (a) a cylinder fixedly attached to the pylon having a top wall and having a first chamber therein;
   (b) a piston reciprocating within said cylinder, said piston having a seal and forming a second chamber between said piston and said cylinder top wall, said first chamber being separated from said second chamber by said seal;
   (c) said piston extending outside said cylinder and being fixedly attached to the socket;
   (d) an intake/exhaust port connected to said second chamber;
   (e) a one-way valve connecting the cavity to the intake/exhaust port; and
   (f) a second one-way valve connecting the intake/exhaust port to atmosphere
   wherein application of the wearer's body weight to said piston moves said piston downwardly within said cylinder, causing air to be drawn out of the cavity and into said second chamber through said one-way valve and said intake/exhaust port, and wherein removal of the wearer's body weight from said piston moves said piston upwardly within said cylinder, forcing air out of said second chamber through said intake/exhaust port and through said second one-way valve to atmosphere.

26. The apparatus of claim 25, said cylinder having a top wall and having an aperture through said top wall, said piston having a stem slidingly engaging said aperture.

27. The apparatus of claim 26, said cylinder top wall further comprising a plurality of tubes each with a closed end and an open end, said open end facing the socket, and said stem further comprising a plurality of projections attached thereto, said projections slidingly engaged within said tubes.

28. The apparatus of claim 25, said shock absorber further comprising a spring biasing said piston toward the socket.

29. The apparatus of claim 25, said shock absorber further comprising compressed air in the first chamber biasing said piston toward the socket.

30. The apparatus of claim 29, further comprising an adjustment valve adapted to vary the pressure of air between said piston and said cylinder.

31. The apparatus of claim 2, wherein said vacuum pump further comprises:
   (a) a housing attached to the socket;

(b) a cylinder having a first chamber therein, said cylinder attached to the pylon;

(c) a piston reciprocating within said cylinder;

(d) said housing having a second chamber therein and said cylinder reciprocating within said second chamber;

(e) first valve means connecting said first chamber to the cavity and to the atmosphere; and (f) second valve means connecting said second chamber to the cavity and to the atmosphere.

32. The apparatus of claim 3, wherein said vacuum pump further comprises:

(a) a cylinder having a hollow core therein, said cylinder attached to the pylon;

(b) a piston reciprocating within said cylinder, said piston having a seal and forming first and second chambers between said piston and said cylinder, said first chamber being separated from said second chamber by said seal;

(c) said piston extending outside said cylinder and being attached to the socket;

(d) an intake/exhaust port connected to said second chamber; and (e) first and second one-way valves connecting the intake/exhaust port to the cavity and to atmosphere, respectively.

33. In a hypobarically-controlled artificial limb for amputees who have a residual limb, the artificial limb having a socket with a volume and shape to receive a substantial portion of the residual limb with a cavity therebetween, a foot, and a pylon between the foot and the socket a weight-activated vacuum pump and shock absorber apparatus attached to the pylon, said vacuum pump and shock absorber apparatus comprising:

(a) a vacuum pump activated by the wearer's body weight and adapted to remove air from the cavity; and (b) a shock absorber cooperating with the vacuum pump to cushion the residual limb against the wearer's body weight during ambulation;

wherein said vacuum pump further comprises:

(i) a housing attached to the socket;

(ii) a cylinder having a first chamber therein, said cylinder attached to the pylon;

(iii) a piston reciprocating within said cylinder;

(iv) said housing having a second chamber therein and said cylinder reciprocating within said second chamber;

(v) first valve means connecting said first chamber to the cavity and to the atmosphere; and (vi) second valve means connecting said second chamber to the cavity and to the atmosphere.

34. In a hypobarically-controlled artificial limb for amputees who have a residual limb, the artificial limb having a socket with a volume and shape to receive a substantial portion of the residual limb with a cavity therebetween, a foot, and a pylon between the foot and the socket a weight-activated vacuum pump and shock absorber apparatus attached to the pylon, said vacuum pump and shock absorber apparatus comprising:

(a) a vacuum pump activated by the wearers body weight and adapted to remove air from the cavity; and (b) a shock absorber cooperating with the vacuum pump to cushion the residual limb against the wearer's body weight during ambulation;

wherein said vacuum pump further comprises:

(i) a cylinder having a hollow core therein, said cylinder attached to the pylon;

(ii) a piston reciprocating within said cylinder, said piston having a seal and forming first and second chambers between said piston and said chamber cylinder, said first being separated from said second chamber by said seal;

(iii) said piston extending outside said cylinder and being attached to the socket;

(iv) an intake/exhaust port connected to said second chamber; and (v) first and second one-way valves connecting the intake/exhaust port to the cavity and to atmosphere, respectively.

* * * * *

UNITED STATES PATENT AND TRADEMARK OFFICE
CERTIFICATE OF CORRECTION

PATENT NO.     : 6,761,742 B2
DATED          : July 13, 2004
INVENTOR(S)    : Carl A. Caspers It is certified that error appears in the above-identified patent and that said Letters Patent is hereby corrected as shown below:

Column 20,
Line 30, delete the word -- chamber -- after "said"
Line 31, add the word -- chamber -- between "first" and "being"

Signed and Sealed this

Seventh Day of September, 2004

JON W. DUDAS
*Director of the United States Patent and Trademark Office*